(12) United States Patent
Fentz et al.

(10) Patent No.: US 8,580,489 B2
(45) Date of Patent: Nov. 12, 2013

(54) USE OF AN ENDOPLASMIN FRAGMENT AND DERIVATIVES THEREOF AS BIOMARKER FOR COLORECTAL ADENOMA AND/OR CARCINOMA; METHOD FOR DETECTION AND TEST SYSTEM

(75) Inventors: Anne-Kristin Fentz, Hamburg (DE); Kerstin David, Hamburg (DE); Hartmut Juhl, Hamburg (DE)

(73) Assignee: Indivumed GmbH, Hamburg (DE)

( * ) Notice: Subject to any disclaimer, the term of this patent is extended or adjusted under 35 U.S.C. 154(b) by 662 days.

(21) Appl. No.: 11/990,598

(22) PCT Filed: Aug. 19, 2005

(86) PCT No.: PCT/EP2005/009005
§ 371 (c)(1),
(2), (4) Date: Jan. 12, 2010

(87) PCT Pub. No.: WO2007/019875
PCT Pub. Date: Feb. 22, 2007

(65) Prior Publication Data
US 2010/0273668 A1 Oct. 28, 2010

(51) Int. Cl.
*C12Q 1/00* (2006.01)
*G01N 33/53* (2006.01)
*G01N 33/567* (2006.01)
*G01N 33/574* (2006.01)

(52) U.S. Cl.
USPC ............... 435/4; 435/7.1; 435/7.21; 435/7.23

(58) Field of Classification Search
None
See application file for complete search history.

(56) References Cited

U.S. PATENT DOCUMENTS

2007/0202496 A1* 8/2007 Beretta ............................. 435/5

FOREIGN PATENT DOCUMENTS

DE 10019967 A1 10/2001
WO WO 2004/057336 A2 7/2004

OTHER PUBLICATIONS

Benedict et al. (J. Exp. Medicine, 2001, 193(1) 89-99).*
Jiang et al. (J. Biol. Chem., 2003, 278(7) 4763-4769).*
Matsushita et al. (FEBS Letters, 1999, vol. 443, pp. 348-352).*
Singh et al. (Glycobiology, 2001, vol. 11, pp. 587-592).*
Greenbaum et al. (Genome Biology, 2003, vol. 4, Issue 9, pp. 117.1-117.8).*
Boyd (The Basic Science of Oncology, 1992, McGraw-Hill, Inc., p. 379).*
Busken, C et al. (Digestive Disease Week Abstracts and Itinerary Planner, 2003, abstract No. 850).*
Krontiris and Capizzi (Internal Medicine, 4th Edition, Editor-in-chief Jay Stein, Elsevier Science, 1994 Chapters 71-72, pp. 699-729).*
Wang et al. (World J. Gatroenterol. Feb. 21, 2005 11(7): 1056-1059).*
Reddy et al. (J. Biol. Chem. 1999 40(1): 28,476-28,483).*
Bando et al. (Euro. J. Neurosci. 2003 18: 829-840).*
Lakshmikuttyamma et al. (Cancer Epidemiology, Biomarkers, & Prevention, Oct. 2004, 13(10): 1604-1609)gb.*
Kaiser (Science, 2006, 313: 1370).*
Breiman, L., Friedman, et al., Classification and Regression Trees, Wadsworth & Brooks/Cole Advanced Books & Software (1984) Monterey, CA.
Albrethsen J., et al., Upregulated Expression of Human Neutrophil Peptides 1,2, and 3 (HNP 1-3) in Colon Cancer Serum and Tumours; A Biomarker Study, BMC Cancer, (2005) 5:8.
Ellington, A. & Szostak, J., Nature, (1990) 346, 818-822.
Tuerk, C. & Gold, L., Science (1990) 249, 505-510.
Posner, M. & Mayer, R., The Use of Serologic Tumor Markers in Gastro Intestinal Malignancies, Hemal Oncol Clin North Am. (1994) 8: 533.
Kudo, S., Gastrointest. Endosc. Clin. N. Am., (1997), 7:87-98.
Stewart, B. & Kleihues, P., World Cancer Report, (2003), 12, 16, 198-199, IARC Press, Lyon.
Di, et al., Cell Research, vol. 10, pp. 115-125 (2000).
Baek, et al., Mol. Pharmacol., vol. 59, No. 4, pp. 901-908 (2001).
Wang, et al., World J. Gastroenterol., vol. 11, No. 7, pp. 1056-1059 (2005).
Chen, et al., Carcinogenesis, vol. 23, No. 1, pp. 123-130 (2002).
Schreiter, et al., Gut, vol. 54, pp. 935-943 (2005).
NCBI Accession Nos. AY040226, AB209534 (May 4, 2006).
Bullen, et al., Medical and Pediatric Oncology, vol. 3, pp. 289-300 (1977).
Yuceyer, et al., International Surgery, vol. 81 pp. 136-139 (1996).
Roboz, et al., Proc. Amer. Assoc. Cancer Res. vol. 45, Abstract 3551 (2004).
Wang, et al., World Journal of Gastroenterology, vol. 11, No. 7, pp. 1056-1058 (2005).
Notice of Reasons of Rejection in Corresponding Japanese Patent Applicatin No. 2008-526379 (Feb. 2, 2010).
Menoret et al., Int. J. Cancer, vol. 56, pp. 400-405, 1994.

(Continued)

*Primary Examiner* — Peter J Reddig
(74) *Attorney, Agent, or Firm* — Elliot M. Olstein; Raymond J. Lillie

(57) ABSTRACT

The present invention is directed to a method for detecting colorectal adenoma and/or colorectal carcinoma comprising the steps: a) providing an isolated sample material which has been taken from an individual, b) determining the level of an endoplasmin fragment or a derivative thereof in said isolated sample material, c) comparing the determined level of an endoplasmin fragment or a derivative thereof with one or more reference values. The invention is further directed to a method for discriminating between colorectal adenoma and colorectal carcinoma as well as to a method for monitoring the development and/or course of colorectal adenoma and/or colorectal carcinoma and/or the treatment of colorectal adenoma and/or colorectal carcinoma. Moreover, the invention is directed to a test system and an array for use in these methods.

30 Claims, 10 Drawing Sheets

(56) References Cited

OTHER PUBLICATIONS

Heike, et al., Int. J. Cancer, vol. 86, pp. 489-493 (2008).

Decision to Grant a Patent on Japanese Patent Application No. 2008-526379, dated Aug. 19, 2011.

* cited by examiner

SEQ ID NO. 1
Sequence of Endoplasmin (grp 94)

```
  1 MRALWVLGLC CVLLTFGSVR ADDEVDVDGT VEEDLGKSRE GSRTDDEVVQ REEEAIQLDG
 61 LNASQIRELR EKSEKFAFQA EVNRMMKLII NSLYKNKEIF LRELISNASD ALDKIRLISL
121 TDENALSGNE ELTVKIKCDK EKNLLHVTDT GVGMTREELV KNLGTIAKSG TSEFLNKMTE
181 AQEDGQSTSE LIGQFGVGFY SAFLVADKVI VTSKHNNDTQ HIWESDSNEF SVIADPRGNT
241 LGRGTTITLV LKEEASDYLE LDTIKNLVKK YSQFINFPIY VWSSKTETVE EPMEEEEAAK
301 EEKEESDDEA AVEEEEEEKK PKTKKVEKTV WDWELMNDIK PIWQRPSKEV EEDEYKAFYK
361 SFSKESDDPM AYIHFTAEGE VTFKSILFVP TSAPRGLFDE YGSKKSDYIK LYVRRVFITD
421 DFHDMMPKYL NFVKGVVDSD DLPLNVSRET LQQHKLLKVI RKKLVRKTLD MIKKIADDKY
481 NDTFWKEFGT NIKLGVIEDH SNRTRLAKLL RFQSSHHPTD ITSLDQYVER MKEKQDKIYF
541 MAGSSRKEAE SSPFVERLLK KGYEVIYLTE PVDEYCIQAL PEFDGKRFQN VAKEGVKFDE
601 SEKTKESREA VEKEFEPLLN WMKDKALKDK IEKAVVSQRL TESPCALVAS QYGWSGNMER
661 IMKAQAYQTG KDISTNYYAS QKKTFEINPR HPLIRDMLRR IKEDEDDKTV LDLAVVLFET
721 ATLRSGYLLP DTKAYGDRIE RMLRLSLNID PDAKVEEEPE EEPEETAEDT TEDTEQDEDE
781 EMDVGTDEEE ETAKESTAEK DEL
```

Figure 1B
Fragments of endoplasmin (grp 94)

SEQ-ID NO.2
EEEAIQLDG LNASQIR

SEQ-ID NO.3
FAFQA EVNR

SEQ-ID NO.4
EEEAIQLDG LNASQIRELR EKSEKFAFQA EVNR

Figure 2

C3 (SEQ ID NO.5)

```
C3 Protein
ID    CO3_HUMAN_2;  parent: CO3_HUMAN
FT    CHAIN        23     1663        Complement C3.
SQ    Sequence    1641 AA;
      SPMYSIITPN  ILRLESEETM  VLEAHDAQGD  VPVTVTVHDF  PGKKLVLSSE  KTVLTPATNH
      MGNVTFTIPA  NREFKSEKGR  NKFVTVQATF  GTQVVEKVVL  VSLQSGYLFI  QTDKTIYTPG
      STVLYRIFTV  NHKLLPVGRT  VMVNIENPEG  IPVKQDSLSS  QNQLGVLPLS  WDIPELVNMG
      QWKIRAYYEN  SPQQVFSTEF  EVKEYVLPSF  EVIVEPTEKF  YYIYNEKGLE  VTITARFLYG
      KKVEGTAFVI  FGIQDGEQRI  SLPESLKRIP  IEDGSGEVVL  SRKVLLDGVQ  NLRAEDLVGK
      SLYVSATVIL  HSGSDMVQAE  RSGIPIVTSP  YQIHFTKTPK  YFKPGMPFDL  MVFVTNPDGS
      PAYRVPVAVQ  GEDTVQSLTQ  GDGVAKLSIN  THPSQKPLSI  TVRTKKQELS  EAEQATRTMQ
      ALPYSTVGNS  NNYLHLSVLR  TELRPGETLN  VNFLLRMDRA  HEAKIRYYTY  LIMNKGRLLK
      AGRQVREPGQ  DLVVLPLSIT  TDFIPSFRLV  AYYTLIGASG  QREVVADSVW  VDVKDSCVGS
      LVVKSGQSED  RQPVPGQQMT  LKIEGDHGAR  VVLVAVDKGV  FVLNKKNKLT  QSKIWDVVEK
      ADIGCTPGSG  KDYAGVFSDA  GLTFTSSSGQ  QTAQRAELQC  PQPAARRRRS  VQLTEKRMDK
      VGKYPKELRK  CCEDGMRENP  MRFSCQRRTR  FISLGEACKK  VFLDCCNYIT  ELRRQHARAS
      HLGLARSNLD  EDIIAEENIV  SRSEFPESWL  WNVEDLKEPP  KNGISTKLMN  IFLKDSITTW
      EILAVSMSDK  KGICVADPFE  VTVMQDFFID  LRLPYSVVRN  EQVEIRAVLY  NYRQNQELKV
      RVELLHNPAF  CSLATTKRRH  QQTVTIPPKS  SLSVPYVIVP  LKTGLQEVEV  KAAVYHHFIS
      DGVRKSLKVV  PEGIRMNKTV  AVRTLDPERL  GREGVQKEDI  PPADLSDQVP  DTESETRILL
      QGTPVAQMTE  DAVDAERLKH  LIVTPSGCGE  QNMIGMTPTV  IAVHYLDETE  QWEKFGLEKR
      QGALELIKKG  YTQQLAFRQP  SSAFAAFVKR  APSTWLTAYV  VKVFSLAVNL  IAIDSQVLCG
      AVKWLILEKQ  KPDGVFQEDA  PVIHQEMIGG  LRNNNEKDMA  LTAFVLISLQ  EAKDICEEQV
      NSLPGSITKA  GDFLEANYMN  LQRSYTVAIA  GYALAQMGRL  KGPLLNKFLT  TAKDKNRWED
      PGKQLYNVEA  TSYALLALLQ  LKDFDFVPPV  VRWLNEQRYY  GGGYGSTQAT  FMVFQALAQY
      QKDAPDHQEL  NLDVSLQLPS  RSSKITHRIH  WESASLLRSE  ETKENEGFTV  TAEGKGQGTL
      SVVTMYHAKA  KDQLTCNKFD  LKVTIKPAPE  TEKRPQDAKN  TMILEICTRY  RGDQDATMSI
      LDISMMTGFA  PDTDDLKQLA  NGVDRYISKY  ELDKAFSDRN  TLIIYLDKVS  HSEDDCLAFK
      VHQYFNVELI  QPGAVKVYAY  YNLEESCTRF  YHPEKEDGKL  NKLCRDELCR  CAEENCFIQK
      SDDKVTLEER  LDKACEPGVD  YVYKTRLVKV  QLSNDFDEYI  MAIEQTIKSG  SDEVQVGQQR
      TFISPIKCRE  ALKLEEKKHY  LMWGLSSDFW  GEKPNLSYII  GKDTWVEHWP  EEDECQDEEN
      QKQCQDLGAF  TESMVVFGCP  N
```

Figure 3A

C3A: 77 amino acids, 9,094 Da , pI 9.7 (SEQ ID NO.6)

ID CO3_HUMAN_5; parent: CO3_HUMAN
FT PEPTIDE 672 748 C3a anaphylatoxin.
SQ Sequence ;
SVQLTEKRMD KVGKYPKELR KCCEDGMREN PMRFSCQRRT RFISLGEACK
KVFLDCCNYITELRRQHARA SHLGLAR

Figure 3B

C3A-desArg: 76 amino acids, pI 9.54 (SEQ ID NO.7)

SVQLTEKRMD KVGKYPKELR KCCEDGMREN PMRFSCQRRT RFISLGEACK
KVFLDCCNYITELRRQHARA SHLGLA

Endoplasmin fragment

Analysis of peak 3,489 [Da] by SELDI-TOF-MS

Analysis of peak 4838 [Da] by SELDI-TOF-MS

Figure 10 A
Figure 10 B
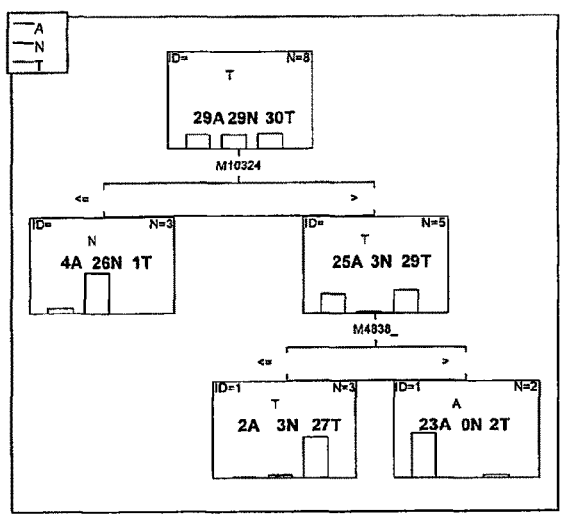
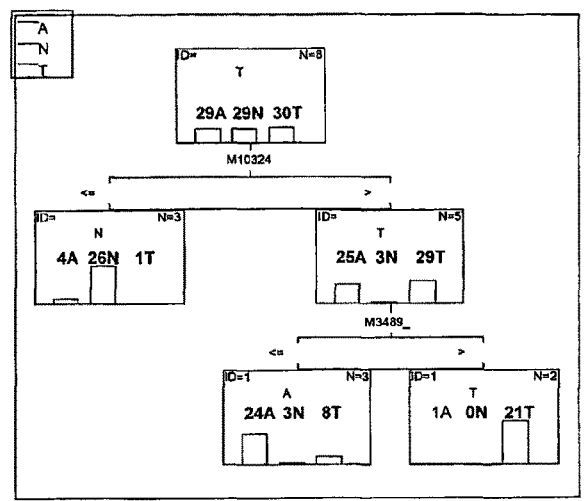

USE OF AN ENDOPLASMIN FRAGMENT AND DERIVATIVES THEREOF AS BIOMARKER FOR COLORECTAL ADENOMA AND/OR CARCINOMA; METHOD FOR DETECTION AND TEST SYSTEM

The present invention relates to the field of detection of colorectal adenoma and/or colorectal carcinoma.

Colorectal carcinoma is the third most frequently diagnosed carcinoma (9.4%) worldwide. In 2003 nearly 945 000 new cases of colorectal carcinoma were diagnosed worldwide and approximately 492 000 people died of this disease. The incidence of colorectal carcinoma is increasing, while the mortality rate of colorectal carcinoma is decreasing. Incidence of colorectal carcinoma increases with age, beginning at around 40 years of age, and it is higher for men than for women (40.6 for men versus 30.6 for women, per 100 000 per year) (World cancer report, 2003, Ed. B W. Stewart and P. Kleihues. IARC Press, Lyon).

In most patients, development of colorectal carcinoma follows a multistep progression from premalignant adenoma to invasive malignancies that have the propensity for metastasis.

So far only unpleasant colorectal screening tests such as colonoscopy have been shown to achieve detection of early stage colorectal carcinoma and its precursors. However, high false negative rates have been observed for flat neoplastic lesions and polypoid lesions smaller than 10 mm diameter (Kudo S. (1997) Gastrointest. Endosc. Clin. N. Am. 7:87-98). Therefore, it would be desirable to have a test system allowing the early detection of colorectal adenoma and/or colorectal carcinoma as well as the specific discrimination between different tumor stages. This would also allow a specific adaptation of the therapy.

The currently known screening tests based on tumor marker detection in blood samples lack the required sensitivity and specificity. For instance, CEA—(Carcinoembryonic antigen)—levels in blood samples have been used to detect colon carcinoma. However, CEA levels are not specifically elevated in colon carcinoma and have been shown to be elevated also in patients with other malignant diseases (e.g., cancers of the stomach, pancreas, breast, and lung) and with various nonmalignant conditions (e.g., alcoholic liver disease, inflammatory bowel disease, heavy cigarette smoking, chronic bronchitis, and pancreatitis). (Posner M R, Mayer R J: The use of serologic tumor markers in gastro intestinal malignancies. Hematol Oncol Clin North Am 8:533, 1994). Further, the CEA-levels are not elevated in colon adenomas. Furthermore, CEA-levels are not suitable to distinguish colorectal adenoma from colorectal carcinoma or different tumor stages.

An object of the invention is to provide means allowing an early detection of colon adenoma and/or colon carcinoma and/or allowing discrimination of different tumor stages.

It is a further object to provide a biomarker which can be used in the detection of colorectal adenoma and/or carcinoma and/or which can be used in the discrimination of different tumor stages.

Another object of the present invention is to provide a test system for detecting colorectal adenoma and/or carcinoma and/or for discrimination of different tumor stages which is cost effective and can be widely used.

Moreover, the test system should be easy to handle.

It is an further object of the present invention to provide a screening system for detecting the effectiveness of compounds which are specific for the treatment of adenoma and/or carcinoma depending on the specific stage of tumors.

The objects underlying the present invention are solved by the use of an endoplasmin fragment or a derivative thereof as a biomarker for the detection of colorectal adenoma and/or colorectal carcinoma in an individual and/or for the discrimination of different tumor stages. The detection can be carried out in vivo and in vitro. Pursuant to a preferred embodiment, the detection is carried out in vitro.

The objects are further solved by a method for detecting colorectal adenoma and/or colorectal carcinoma comprising the steps:
  a) providing an isolated sample material which has been taken from an individual,
  b) determining the level of an endoplasmin fragment or a derivative thereof in said isolated sample material,
  c) comparing the determined level of an endoplasmin fragment or a derivative thereof with one or more reference values.

The objects are further solved by a method for discriminating colorectal adenoma and colorectal carcinoma and/or for discriminating further tumor states comprising the steps:
  a) providing an isolated sample material which has been taken from an individual,
  b) determining the level of an endoplasmin fragment or a derivative thereof in said isolated sample material,
  c) comparing the determined level of an endoplasmin fragment or a derivative thereof with one or more reference values.

The objects are also solved by a method for monitoring the development and/or the course and/or the treatment of colorectal adenoma and/or colorectal carcinoma comprising the steps:
  a) providing an isolated sample material which has been taken from an individual,
  b) determining the level of an endoplasmin fragment or a derivative thereof in said isolated sample material,
  c) comparing the determined level of an endoplasmin fragment or a derivative thereof with one or more reference values.

In a preferred embodiment the effectiveness of a surgical or therapeutical procedure is controlled in order to decide as to whether the colorectal adenoma and/or colorectal carcinoma is completely removed. In another embodiment the therapy of a colorectal adenoma and/or colorectal cancer patient by treating the patient with one or more chemical substances, antibodies, proteins, peptides, small molecular drug, antisense-RNA, radiation, e.g. X-rays, or combinations thereof is controlled in order to control the effectiveness of the treatment.

The objects underlying the invention are solved by providing a test system for detecting colorectal adenoma and/or colorectal cancer and/or for the differentiation of different tumor stages in a sample of an individual comprising:
  a) an antibody or a receptor which binds to an epitope of an endoplasmin fragment or a derivative thereof,
  b) a solid support which supports said antibody or receptor,
  c) a reagent for detecting the binding of said epitope of an endoplasmin fragment or a derivative thereof to said antibody or receptor.

The objects of the invention are furthermore solved by the provision of an array comprising detection molecules for detecting of colorectal adenoma and/or colorectal carcinoma cancer and/or for the differentiation of different tumor stages in an individual comprising as detection molecule:
  a) a nucleic acid probe immobilized to a solid support for binding to and detecting mRNA encoding an endoplasmin fragment or a derivative thereof, or b) an antibody immobilized to a solid support for binding to and detecting of an epitope of an endoplasmin fragment or a derivative thereof, or c) a receptor immobilized to a solid support for binding to and detecting of an epitope of an endoplasmin fragment or a derivative thereof, wherein preferably different amounts of detection molecules are immobilized to the solid support to increase the accuracy of the quantification.

The nucleic acid probe is for example selected from the group consisting of single-stranded or double-stranded DNA or RNA, aptamers and combinations thereof. Aptamers are single-stranded oligonucleotides that assume a specific, sequence-dependent shape and bind to protein targets with high specificity and affinity. Aptamers are identified using the SELEX process (Tuerk C. and Gold L. (1990) Science 249: 505-510; Ellington A D. and Szostak J W (1990) Nature 346, 818-822).

The objects are furthermore solved by a method for determining whether a compound is effective in the treatment of colorectal adenoma and/or colorectal carcinoma cancer and/or for the differentiation of different tumor stages comprising the steps:

a) treating of a colorectal adenoma or colorectal carcinoma patient with a compound, b) determining the level of an endoplasmin fragment or a derivative thereof in a sample material of said patient, and c) comparing the determined level of an endoplasmin fragment or a derivative thereof with one or more reference values.

Preferred embodiments are specified in dependent claims.

According to the present invention the term "sample material" is also designated as "sample".

Pursuant to the present invention the term "biomarker" is meant to designate a protein or protein fragment or a nucleic acid which is indicative for the incidence of the colorectal adenoma and/or colorectal carcinoma. That means the "biomarker" is used as a means for detecting colorectal adenoma and/or colorectal carcinoma.

The term "individual" or "individuals" is meant to designate a mammal. Preferably, the mammal is a human being such as a patient.

The term "healthy individual" or "healthy individuals" is meant to designate individual(s) not diseased of colorectal adenoma and/or colorectal carcinoma. That is to say, the term "healthy individual(s)" is used only in respect of the pathological condition of colorectal adenoma and/or colorectal carcinoma and does not exclude the individual to suffer from diseases other than colorectal adenoma and/or colorectal carcinoma.

The term "discrimination of different tumor stages" according to the present invention means the discrimination of colorectal adenoma versus colorectal carcinoma and/or the discrimination of different tumor stages, e.g. TNM I, II, III and IV.

The term "derivative thereof" is meant to describe any modification on DNA, mRNA or protein level comprising e.g. the truncated gene, fragments of said gene, a mutated gene, or modified gene or the respective gene products thereof. The term "derivatives thereof" includes nucleic acid sequences, such as DNA, RNA, mRNA or protein sequences or peptide sequences. The derivative can be a modification which is an result of a deletion, substitution or insertion in the gene. The gene modification can be a result of the naturally occurring gene variability. The term "naturally occurring gene variability" means modifications which is not a result of genetic engineering. The derivative can be a result of the processing of the gene or gene product within the body and/or a degradation product. The modification on protein level can be due to enzymatic or chemical modification within the body. For example the modification can be a glycosylation or phosphorylation or farnesylation.

The term "endoplasmin fragment or a derivative thereof" as used in the present invention also comprises mutated endoplasmin fragments or modified endoplasmin fragments or fragments of modified endoplasmin. The modification of the "endoplasmin fragment" can be due to enzymatic or chemical modification.

The terms "tumor" and "cancer" are interchangeably used and have the same meaning.

In one embodiment the endoplasmin fragment or derivative thereof is a protein comprising an N-terminal fragment or a C-terminal fragment of endoplasmin. The term N-terminal fragment or C-terminal fragment is not to be understood in that these sequence comprise the complete N-terminus or C-terminus of endoplasmin, respectively, but that the fragment is generated from the N-terminal or C-terminal region of endoplasmin.

The fragment can also be generated from a middle part of the protein sequence of endoplasmin.

The sequence length of the fragment of endoplasmin (SEQ ID NO. 1) must be sufficiently long to be specific for endoplasmin. It has been shown that fragments of endoplasmin comprising at least 7 contiguous amino acids, preferably at least 8 contiguous, amino acids of the sequence of endoplasmin (SEQ ID NO. 1) are highly specific for endoplasmin. Pursuant to a preferred embodiment of the invention the fragment comprises at least 9 contiguous amino acids of endoplasmin (SEQ ID NO. 1).

A specific cleavage of the full-length endoplasmin (SEQ ID NO. 1) which is also designated as grp94 leads to two fragments of about 10-14 kDa and 80 kDa. It is assumed that the endoplasmin-cleavage is induced by Calpain (FIG. 4).

In one embodiment of the invention, the endoplasmin fragment comprises a C-terminal fragment having a molecular weight of about 80 kDa or the N-terminal fragment having a molecular weight of about 10 to 14 kDa. According to another embodiment of the invention the fragments having a molecular weight of about 10 to 14 kDa or about 80 kDa are induced by cleavage by Calpain.

In an embodiment of the invention the endoplasmin fragment comprises a part of the sequence SEQ-ID-NO.1. In a preferred embodiment of the invention the endoplasmin fragment comprises a N-terminal fragment. Preferably the fragment comprises the peptide sequence SEQ ID-NO. 2 and/or the peptide sequence SEQ-ID NO. 3. Pursuant to another embodiment of the invention the fragment comprises the peptide sequence SEQ-ID NO. 4.

In another embodiment of the invention the endoplasmin fragment has a molecular weight of 10 to 14 kDa, more preferably of 10.3 kDa.

In a further embodiment of the invention the endoplasmin fragment is a peptide or protein which is or includes an amino acid sequence having at least 80%, preferably at least 90%, more preferably at least 95% sequence identity with SEQ ID NO. 2, SEQ ID NO. 3 or SEQ ID NO. 4 (FIG. 1) and which is able to specifically detect colorectal adenoma and/or colorectal carcinoma.

Pursuant to another embodiment of the invention the endoplasmin fragment has an amino acid sequence having at least 80%, preferably at least 90%, more preferably at least 95% sequence identity with SEQ ID NO. 1 based on the sequence of the fragment.

Glucose-related proteins (grps) are a group of highly conserved proteins synthesized after stress induction. Grps act as molecular chaperones helping to transport, fold and process their respective target proteins. Immunohistochemical staining detects grp94 mainly in the cytoplasm. Grp94 is also designated as endoplasmin. Grp94 (endoplasmin) exhibits the dual properties of a luminal protein and an integral protein, suggesting that it exists in two different forms within the endoplasmic reticulum.

The term "epitope" is meant to designate any structural element of a protein or peptide or any proteinaceous structure allowing the specific binding of an antibody, an antibody fragment, a protein or peptide structure or a receptor.

The methods of the present invention are carried out with sample materials such as body fluids or tissue samples which already have been isolated from the human body. Preferably, the sample material is a tissue sample. Subsequently the sample material can be fractionated and/or purified. It is for example possible, to store the sample material to be tested in a freezer and to carry out the methods of the present invention at an appropriate point in time after thawing the respective sample material.

It has been surprisingly discovered by the present inventors that an endoplasmin fragment or a derivative thereof can be used as a biomarker, preferably as an early biomarker, for the detection of colorectal adenoma and/or carcinoma.

The inventors have now surprisingly found that the protein levels of endoplasmin fragments or derivatives thereof in a sample material such as a tissue sample or a body fluid are elevated in individuals having colorectal adenoma and/or carcinoma. Furthermore, the inventors have surprisingly found that the endoplasmin fragment protein level or a derivative thereof in a tissue sample or a body fluid can be used to distinguish healthy people from people with colorectal adenoma and/or carcinoma as well as colorectal adenoma from colorectal carcinoma. Furthermore, the level of the endoplasmin fragment can be used to discriminate between different tumor stages, e.g. TNM I, II, III and/or IV. The endoplasmin fragment is a specific biomarker which can be used to discriminate colorectal adenoma and colorectal carcinoma and/or different tumor stages. The different tumor stages can be for example TNM I, II, III and/or IV. The endoplasmin fragment is a selective and specific marker which can be used to confirm the diagnosis obtained by histopathology.

The inventors have, however, also found that an elevated level of complete endoplasmin in the sample material such as tissue or biological fluids, e.g. serum or plasma, is specific for colorectal adenoma. Therefore, an elevated level of the complete endoplasmin is also indicative for colorectal adenoma. In view of that, all explanations given above or below apply for complete endoplasmin respectively.

However, the inventors have also surprisingly found, that an elevated level of fragments of endoplasmin in a sample material such as tissue or a body fluid is a much more specific and sensitive biomarker for colorectal adenoma and/or carcinoma.

Pursuant to the present invention, sample material can be tissue, cells or a body fluid. The sample material can be a body fluid such as blood, blood plasma, blood serum, bone marrow, stool, synovial fluid, lymphatic fluid, cerebrospinal fluid, sputum, urine, mother milk, sperm, exudate and mixtures thereof. In a embodiment of the invention the body fluids are fractionated by chromatography.

Preferably, the body fluid has been isolated before carrying out the methods of the present invention. The methods of the invention are preferably carried out in vitro by a technician in a laboratory.

According to a preferred embodiment of the invention, the level of endoplasmin fragment is measured in blood plasma, blood serum or urine. Blood serum can be easily obtained by taking blood from an individual to be medically examined and separating the supernatant from the clotted blood.

The level of the endoplasmin fragment or a derivative thereof is higher with progressive formation of colorectal adenoma. The colorectal adenoma is a benign neoplasma which may become malign. When developing colorectal cancer from benign colorectal adenoma, the level of the endoplasmin fragment or a derivative thereof in body fluids, preferably blood serum, further increases.

After transformation of colorectal adenoma into colorectal cancer, the pathological condition of the afflicted individual can be further exacerbated by formation of metastasis. The higher levels of the endoplasmin fragment are correlated with the incidence of colorectal adenoma and/or carcinoma and/or metastasis.

The present invention provides an early stage biomarker which allows to detect the neoplastic disease at an early and/or still benign stage and/or an early tumor stage. Early detection enables the physician to timely remove the colorectal adenoma and dramatically increases the chance of the individual to survive.

Moreover, the present invention allows to monitor the level of an endoplasmin fragment or a derivative thereof in a body fluid such as blood serum over an extended period of time, such as years.

The long term monitoring allows to differentiate between colorectal adenoma and colorectal carcinoma. The level of an endoplasmin fragment or a derivative thereof can be routinely checked in body fluid, for example, once or twice a year. If an increase of the level of an endoplasmin fragment or a derivative thereof is detected this can be indicative for colorectal adenoma. A further increase of the level of an endoplasmin fragment or a derivative thereof can then be indicative for the transformation into malignant colorectal carcinoma.

Moreover, the course of the disease and/or the treatment can be monitored. If the level of an endoplasmin fragment or a derivative thereof further increases, for example after removal of the colorectal adenoma, this can be indicative for exacerbation of the pathological condition.

That means, the level of an endoplasmin fragment or a derivative thereof is a valuable clinical parameter for detecting and/or monitoring of colorectal adenoma and/or colorectal carcinoma. The level of an endoplasmin fragment or a derivative thereof in body fluids increases after incidence of colorectal adenoma. Therefore, the level of an endoplasmin fragment or a derivative thereof is an important clinical parameter to allow an early diagnosis and, consequently, an early treatment of the disease. Furthermore, the level of an endoplasmin fragment can be used to check the efficiency of surgery and/or other therapy.

The method of the invention for detection of colorectal adenoma and/or colorectal carcinoma and/or for discriminating between different tumor stages comprises the step of providing an isolated sample material which has been taken from an individual, then determining the level of an endoplasmin fragment or a derivative thereof in the isolated sample material, and finally comparing the determined level of an endoplasmin fragment or a derivative thereof with one or more reference values. In one embodiment, one or more further biomarker(s) is/are additionally detected in an isolated sample material which has been taken from an individual, the level of the biomarker(s) is/are determined and compared with one or more reference value(s).

The reference value can be calculated as the average level of an endoplasmin fragment or a derivative thereof determined in a plurality of isolated samples of healthy individuals or individuals suffering from colorectal adenoma and/or colorectal carcinoma. This reference value can either be established from healthy persons covering a range to be considered as normal, or a range which is considered to be elevated from patients who suffer from colorectal adenoma and/or colorectal carcinoma. Usually, the reference values are given as a range of reference values. Therefore, the term reference value and range of reference values as used in the present invention are defined to have the same meaning.

A specific value within a range of reference values can then be indicative for healthy condition or the pathological condition of colorectal adenoma and/or colorectal carcinoma. This range of reference values can be established by taking a statistically relevant number of tissue samples or body fluid samples, such as serum samples, of healthy individuals and of individuals suffering from colon adenoma and/or colon carcinoma as it is done for any other medical parameter range such as, e.g., blood sugar. The reference value for a healthy condition can also be obtained from healthy tissue of a colorectal adenoma and/or colorectal tumor patient.

Preferably, two reference values are calculated which are designated as negative control and positive control 1. The reference value of the negative control is calculated from healthy individuals or healthy tissue of colorectal adenoma and/or colorectal tumor patients and the positive control is calculated from individuals suffering from colorectal adenoma or colorectal carcinoma. More preferably, three reference values are calculated which are designated as negative control and positive control 1 and positive control 2. Positive control 1 can be calculated from individuals suffering from colorectal carcinoma and positive control 2 can be calculated from colorectal adenoma.

In an another embodiment of the present invention, the reference values can be individual reference values calculated as the average level of an endoplasmin fragment or a derivative thereof determined in a plurality of isolated samples taken from the individual over a period of time.

When monitoring the level of an endoplasmin fragment or a derivative thereof over an extended period of time, such as months or years, it is possible to establish an individual average level. The level of an endoplasmin fragment or a derivative thereof can be measured, for example, from the same blood serum sample when measuring blood sugar and can be used to establish an individual calibration curve allowing to specifically detect any individual increase of the level of an endoplasmin fragment or a derivative thereof.

The reference value for further biomarkers can also be calculated in the same way as described for endoplasmin. The average levels of the endoplasmin fragment or further biomarkers may be the mean or median level.

In another aspect the present invention further provides a test system for detecting colorectal adenoma and/or colorectal carcinoma in an isolated sample material of an individual. The test system is based either on the specificity of an antibody or a receptor to specifically bind to an epitope or a suitable structural element of an endoplasmin fragment or a derivative thereof. A receptor can be any structure able to bind specifically to an endoplasmin fragment or a derivative thereof. The receptor can be, for example, an antibody fragment such as an Fab or an F(ab')$_2$ fragment or any other protein or peptide structure being able to specifically bind to an endoplasmin fragment or a derivative thereof. The receptor can also be an aptamer specifically binding to an endoplasmin fragment or a derivative thereof.

The antibody, antibody fragment or receptor is bound to a solid support such as, e.g., a plastic surface or beads to allow binding and detection of an endoplasmin fragment or a derivative thereof. For example, a conventional microtiter plate can be used as a plastic surface. The detection of the binding of an endoplasmin fragment or a derivative thereof can be effected, for example, by using a secondary antibody labelled with a detectable group. The detectable group can be, for example, a radioactive isotop or an enzyme like horseradish peroxidase or alkaline phosphatase detectable by adding a suitable substrate to produce, for example, a colour or a fluorescence signal.

The test system can be an immunoassay such as an enzyme-linked immunosorbentassay (ELISA) or an radio immunoassay (RIA) or luminescence immunossay (LIA). However, any other immunological test system using the specificity of antibodies or fragments of antibodies can be used such as Western blotting or immuno precipitation.

The present invention also provides an array comprising detection molecules for detecting colorectal adenoma and/or colorectal carcinoma in an individual, wherein the detection molecule can be a nucleic acid probe immobilized on a solid support for binding to and detecting of mRNA encoding endoplasmin fragments, mutations, variants or derivatives thereof, or an antibody immobilized on a solid support for binding to and detecting of an epitope of an endoplasmin fragment or a derivative thereof, or a receptor immobilized on a solid support for binding to and detecting an epitope of an endoplasmin fragment or a derivative thereof. Preferably, the array comprises further detection molecules for biomarkers for detecting colorectal adenoma and colorectal carcinoma. Preferably, the nucleic acid probe comprises nucleic acid sequences selected from the group consisting of the nucleic acid sequences corresponding to SEQ-ID-NO.2 and/or SEQ-ID-NO.3 or SEQ-ID-NO.4. Alternatively, the present invention also comprises an inverse array comprising patient samples immobilized on a solid support which can be detected by the above defined detection molecules.

Preferably the array comprises detection molecules which are immobilized to a solid surface at identifiable positions.

The term "array" as used in the present invention refers to a grouping or an arrangement, without being necessarily a regular arrangement. An array comprises preferably at least 2, more preferably 5, most preferably 10 different sets of detection molecules. Preferably, the array of the present invention comprises at least 50 sets of detection molecules, further preferred at least 100 sets of detection molecules. Pursuant to another embodiment of the invention the array of the present invention comprises at least 500 sets of detection molecules. The detection molecule can be for example a nucleic acid probe or an antibody or a receptor as already described above.

The nucleic acid probe can be any natural occurring or synthetic oligonucleotide, aptamers as well as cDNA, cRNA and the like.

The described array can be used in a test system according to the invention. The term "array" as used in the present invention relates to both macroarrays and microarrays.

Pursuant to another embodiment of the invention, the level of an endoplasmin fragment or a derivative thereof is determined by mass spectroscopy.

Mass spectroscopy allows to specifically detect an endoplasmin fragment or a derivative thereof via its molecular weight and to quantify the amount of an endoplasmin fragment or a derivative thereof very easily.

Any suitable ionization method in the field of mass spectroscopy known in the art can be employed to ionize the endoplasmin fragment or a derivative thereof molecule, fragments, mutations, variants or derivatives thereof. The ionization methods comprise electron impact (EI), chemical ionization (CI), field ionization (FDI), electrospray ionization (ESI), laser desorption ionization (LDI), matrix assisted laser desorption ionization (MALDI) and surface enhanced laser desorption ionization (SELDI).

Any suitable detection method in the field of mass spectroscopy known in the art can be employed to determine the molecular mass of an endoplasmin fragment or a derivative thereof. The detection methods comprise quadrupol mass spectroscopy (QMS), fourier transform mass spectroscopy (FT-MS) and time-of-flight mass spectroscopy (TOF-MS).

Preferably, the mass spectroscopy is a surface enhanced laser desorption ionization-time of flight-mass spectroscopy (SELDI-TOF-MS). Before carrying out a SELDI-TOF-MS, the endoplasmin fragment or a derivative thereof in the isolated sample is preferably immobilized on a chip or solid support with an activated surface. The activated surface comprises preferably immobilized antibodies against an endoplasmin fragment or a derivative thereof such as, for example, rabbit polyclonal-antibodies. After binding of the endoplasmin fragment or a derivative thereof to the antibodies, a time-of-flight analysis in a SELDI-TOF mass spectrometer is carried out, which delivers intensity signals for determination of the endoplasmin fragment or a derivative thereof level.

Moreover, mass spectroscopy allows to simultaneously detect other proteins which can have a relevance with respect to the detection of colorectal adenoma and/or colorectal cancer.

In an embodiment of the present invention the sensitivity and/or specificity of the detection of colorectal adenoma and/or colorectal carcinoma is enhanced by the additional detection of one or more further biomarkers.

Preferably, the sensitivity and specifity of the methods, arrays, test systems and uses according to the present invention are increased by the combination of detecting an endoplasmin fragment and derivatives thereof as well as alpha-defensin 1, 2 or 3 or derivatives thereof.

The term "alpha-defensin 1, 2, 3 or a derivative thereof" as used in the present invention also comprises truncated alpha-defensin 1, 2 or 3, fragments of alpha-defensin1, 2 or 3, mutated alpha-defensin 1, 2 or 3, or modified alpha-defensin 1, 2 or 3. The modification of "alpha-defensin 1, 2 or 3" can be due to enzymatic or chemical modification. alpha-defensins 1, 2 and 3 are also designated as human neutrophil peptides (HNP) 1, 2 and 3, respectively. The three peptides have mass/charge ratios (m/z) of 3445±10, 3374±10 and 3489±10.

HNP 1-3 peptides are part of the defensin family of peptides which are fundamental components of the immune system and have the capacity to kill/inactivate a broad range of pathogens. Defensins are also known to function as regulators of both the innate and the adaptive immune system.

Previous studies indicate that HNP 1-3 expression in tumors primarily originates from tumor invading eosinophils and neutrophils. However, it can also be produced by cancer cells (e.g., bladder cancer cells).

(Albrethsen J, Bogebo R, Gammeltoft S, Olsen J, Winther B, Raskov H. *Upregulated expression of human neutrophil peptides* 1, 2 and 3 (*HNP* 1-3) *in colon cancer serum and tumours: a biomarker study.* BMC Cancer. 2005, 5:8.)

In a further embodiment of the present invention the sensitivity and/or specificity of the detection of colorectal adenoma and/or colorectal carcinoma and/or of the discrimination of different tumor stages can be enhanced by detection of an endoplasmin fragment in combination with one or more further biomarker(s) selected from the group consisting of alpha-defensin 1, 2 or 3, transthyretin, p53, C3a, CEA (carcinoembryonic antigen), CA 19-9, CA 15-3, CA-125, Kras, β-Catenin, Her-2/neu, C-reactive protein plasma and derivatives thereof and mutations in E-cadherin, MSH2, MSH3, MLH1, PMS1, PMS2, MSH6 genes and microsatellite instability of MHL1 or MSH2 and SNPs (single nucleotide polymorphysm) and combinations thereof.

Another biomarker for colorectal adenoma and/or carcinoma may comprise a protein or polypeptide having a molecular weight of 4,838±25 Da, preferably 4,838±10 Da. In a preferred embodiment the endoplasmin fragment and the protein or polypeptide having a molecular weight of 4,838±25 Da, preferably 4,838±10 Da are used both to detect colorectal adenoma and/or carcinoma.

In one embodiment a fragment of endoplasmin or a derivative thereof in combination with C3a or a derivative and/or transthyretin or a derivative thereof are used as biomarkers to detect colorectal adenoma and/or carcinoma and/or to discriminate different tumor stages.

The term "transthyretin or a derivative thereof" as used in the present invention also comprises truncated transthyretin, fragments of transthyretin, mutated transthyretin, or modified transthyretin. The modification of "transthyretin" can be due to enzymatic or chemical modification. Moreover, the term "transthyretin" is also used to designate monomeric or multimeric forms of transthyretin. For example, the term "transthyretin" especially covers the monomeric protein chain usually being part of the homotetrameric protein transthyretin.

Transthyretin is also designated as prealbumin. Transthyretin is a tetrameric protein having a molecular weight of about 54,000 Da that is synthesized mainly in the liver Transthyretin is normally a homotetramer comprising four protein chains having each a molecular weight of about 14,000 Da. Using mass spectroscopy the inventors have detected several variants of the transthyretin protein chains having a molecular weight of inter alia 13,776 Da, 13,884 Da or 14,103 Da. The inventors have found out that especially the level of molecular variants of transthyretin having a molecular weight of 13,776 Da and 13,884 Da is decreased in a body fluid such as serum in case of incidence of colorectal adenoma and/or colorectal carcinoma.

The term "C3a or a derivative thereof" as used in the present invention also comprises truncated C3a, fragments of C3a, mutated C3a, modified C3a or the precursor C3 (FIG. 2, SEQ ID NO.5) or fragments of C3. In one embodiment the derivative has or comprises a protein sequence having an identity of at least 80%, preferably of at least 90%, more preferably of at least 98% with the sequence SEQ-ID-NO. 6 (FIG. 3A, SEQ ID NO. 6).

The modification of "C3a" can be due to enzymatic or chemical modification. In particular, the term C3a or a derivative thereof especially comprises a truncated C3a-protein preferably having a molecular weight in the range of 8,950±25 Da; more preferably in the range of 8,950±20 Da. In a preferred embodiment the truncated C3a-protein has a molecular weight of 8,939 Da. Preferably, the C3a-protein has no C-terminal Arginin and optionally a molecular weight in the range of 8,950±20 Da. In one embodiment the C3a derivative is C3a-desArg (FIG. 3B, SEQ ID NO. 7). In one embodiment the C3a derivative is obtained by cleavage of C3a by mastcell-chymase. In another embodiment the C3a is obtained by cleavage of C3 by C3-convertase. The present invention also includes combination of the aforementioned embodiments.

C3a belongs to the group of anaphylatoxins. C3a, C4a and C5a are proteolytic products of serine proteases of the complement system. C3a (SEQ-ID-NO.6) is derived from the third component (C3) (SEQ-ID-NO.5) of the blood complement system during complement activation. C3a is a hormone with local effectiveness. Approximately 40% of the amino acid residues in C3a are involved in a helical conformation. Serum anaphylatoxins are involved in a variety of cellular immune responses, as well as being potent proinflammatory agents. C3a produces powerful effects on blood vessel walls, contraction of smooth muscle and an increase in vascular permeability. The C-terminal arginine in C3a is of fundamental importance for its biological activity. Anaphylatoxins are regulated by carboxypeptidase N (anaphylatoxin inactivator), which removes within seconds the carboxyterminal arginine. This mechanism converts the intact anaphylatoxin into a less active C3a-desArg form (SEQ ID NO.7).

This allows the detection of colorectal adenoma and/or colorectal carcinoma with an increased sensitivity and/or specificity and/or the discrimination of different tumor states. Further, the methods of the present invention will be well accepted by the patients since these methods are not as unpleasant as a colonoscopy. Pursuant to the present invention sample material isolated from the individual, which can be a tissue specimen or a biological fluid, e.g. plasma or serum, is screened with the methods of the invention. The sample material can be obtained, for example, by taking blood or by a biopsy.

The sensitivity and specificity are defined as follow:

The sensitivity is the number of true positive detected patients (%) with regard to the number of all patients (100%). The patients can be individuals having colorectal adenoma and/or colorectal carcinoma.

The specificity is the number of true negative detected individuals (%) with regard to the number of all healthy individuals (100%).

The sensitivity and specificity can be alternatively defined by the following formulas:

|      |   | diagnosis |    |
|------|---|-----------|----|
|      |   | +         | -  |
| test | + | TP        | FP |
|      | - | FN        | TN |

TP: True positive (test positiv, diagnosis correct);
FP: False positive (test positiv, diagnosis incorrect);
TN: True negative (test negative, diagnosis correct);
FN: False negative (test negative, diagnosis incorrect);

The sensitivity is calculated by the following formula:

TP/(TP+FN)

and the specificity is calculated by the following formula:

TN/(TN+FP)

The result of each analysis group, which is selected from TP, FP, TN, FN, is calculated for a plurality of isolated samples selected from the group consisting of healthy individuals, colorectal adenoma patients and/or colorectal carcinoma patients. TP, FP, TN, FN relates to the number of individuals that are correlated with the status true positive, false positive, true negative, false negative, respectively.

The methods of the present invention can be carried out in combination with other diagnostic methods for detection of colorectal adenoma and/or colorectal carcinoma to increase the overall sensitivity and/or specificity. The detection of an endoplasmin fragment allows a very early detection of colorectal adenoma and can therefore be used as an very early biomarker. Furthermore, the detection of an endoplasmin fragment allows the discrimination of different tumor stages.

Preferably, the methods of the present invention are carried out as an early detection and/or monitoring method. If the results of the methods of the present invention should indicate the incidence of colorectal adenoma and/or colorectal adenoma in samples of body fluid, further examinations such as colonoscopy could be carried out. If the results obtained by histochemistry with tissue samples indicate the incidence of colorectal adenoma and/or colorectal adenoma the level of an endoplasmin fragment optionally in combination with a further biomarker should be analysed, in order to discriminate the different tumor stages.

The present invention further provides a method for determining whether a compound is effective in the treatment colorectal adenoma and/or colorectal carcinoma. Furthermore, the present invention provides a method for selecting a specific compound which is useful for treating a specific tumor stage.

Preferably, the method for determining whether a compound is effective in the treatment of colorectal adenoma and/or colorectal carcinoma and/or for the treatment of specific tumor stages comprises the steps of:

a) treating of a colorectal adenoma or colorectal carcinoma patient with a compound
  b) determining the level of an endoplasmin fragment or a derivative thereof in a sample material of said patient
  c) comparing the determined level of an endoplasmin fragment or a derivative thereof with one or more reference values.

The term "patient" as used in the present application covers humans as well as non-human beings such as animals. The animals are preferably selected from the group consisting of rodents, e.g. mouse, rat, hamster, and other animals, e.g. guinea-pig, rabbit, hare, dog and pig.

These animals can be used to specifically induce certain disease states, like colorectal adenoma and colorectal carcinoma, for research purposes. The induction of said disease states can, for example, be effected by treatment of the animals, for example, with radioactive or chemical substances known to induce colorectal cancer or colorectal adenoma disease state. The disease states can also be induced using viral transfection systems. It is also possible to use genetically modified animals, in which one or more specific gene function(s) has/have been altered, or knock-out animals such as knock-out mice in which a specific gene function has been deleted.

The compound for treatment of colorectal adenoma and/or colorectal carcinoma can be one or more chemical substances, antibody(ies), protein, peptide(s), small molecular drugs or antisense mRNA(s). Alternatively, instead of one or more compounds irradiation can be used alone or in combination with one or more compounds.

The level of an endoplasmin fragment or a derivative thereof in a sample material of said patient can be determined by the above described detection techniques.

The following figures and example are given for illustrative purposes only. The invention is not to be construed to be limited to the following examples.

FIGURES

FIG. 1 shows the protein sequence of endoplasmin (SEQ-ID NO.1) in FIG. 1A, and three peptide sequences which are each part of the N-terminal endoplasmin fragment (SEQ ID NO. 2, 3 and 4) in FIG. 1B.

FIG. 2 shows the C3 protein sequence (SEQ ID NO. 5).

FIG. 3 shows the C3a protein sequence (SEQ ID NO. 6) in FIG. 3A, and the C3a-desArg protein sequence (SEQ ID NO. 7) in FIG. 3B.

Figure 7:
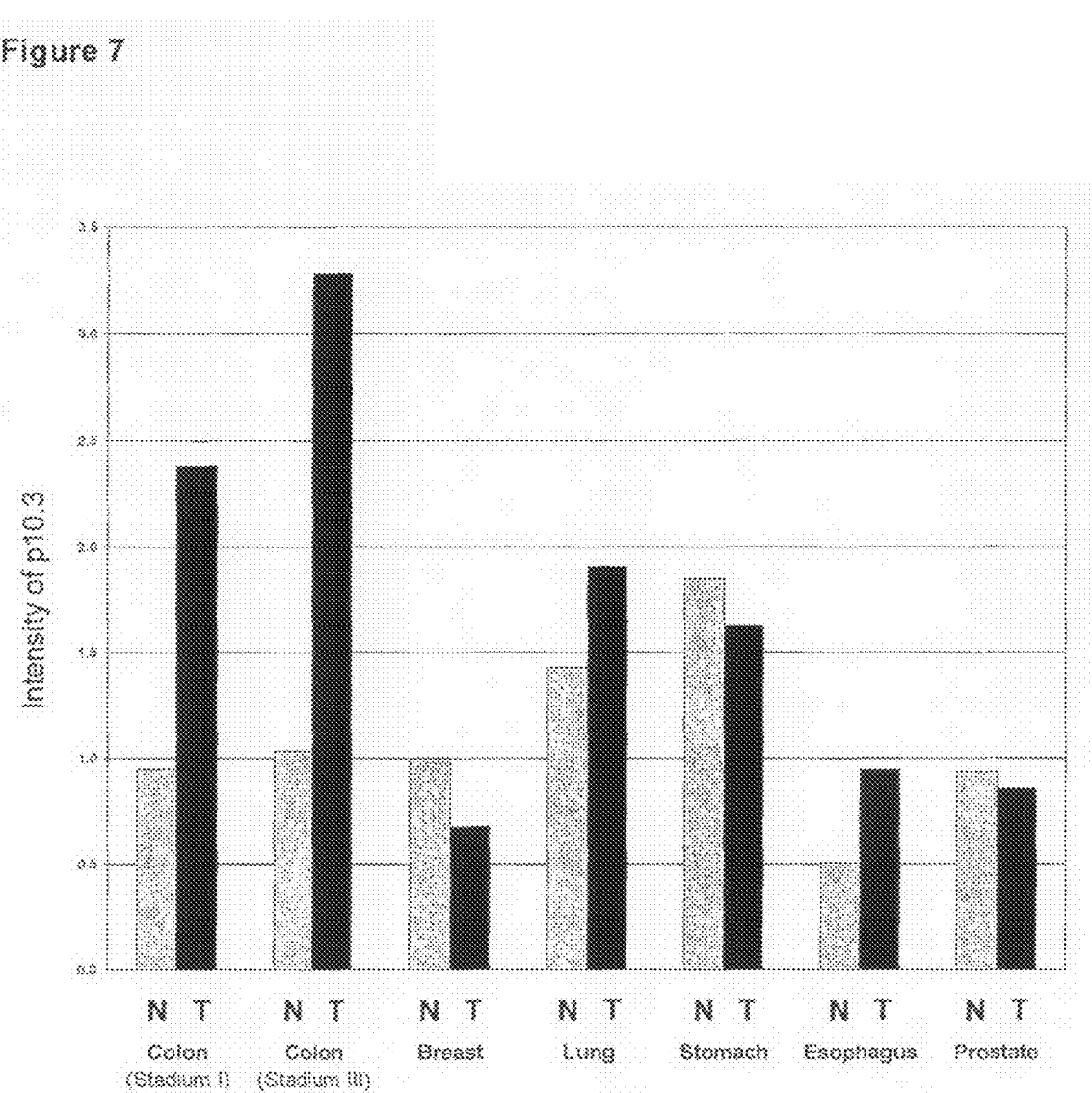

FIG. 7 shows the detection of p10.3 in different cancer types by SELDI TOF MS. The expression level of p10.3 was significant lower in analysed samples of stomach, esophageal, lung, prostate and breast cancer compared to different colon carcinoma stages. The lysates were analysed on a SAX Protein Chip®Array. The difference in expression levels of p10.3 between normal and tumor tissues are statistically significant. N=normal tissue, T=cancer tissue.

Figure 8:
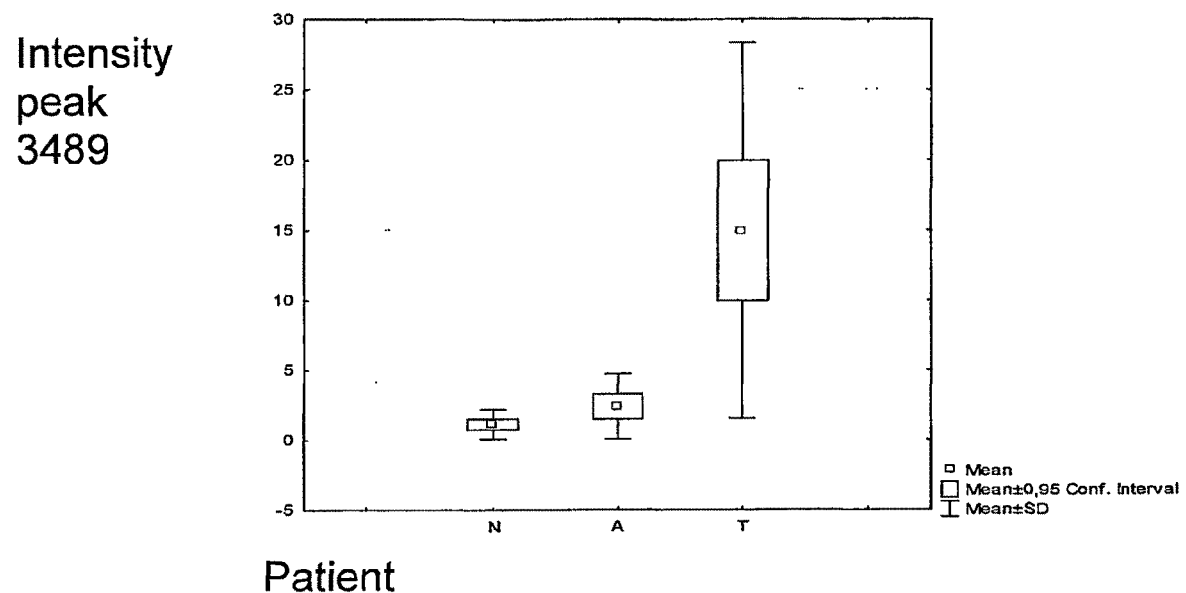

FIG. 8 shows SELDI-TOF-MS protein profiles of lysates from normal colon, adenoma and cancer tissue. The peak intensities of p3489 (a member of the alpha-defensin family, p3.4) increase significantly in tissue from colorectal adenoma to cancer patients. N=normal tissue, A=adenoma tissue, T=cancer tissue.

Figure 9:
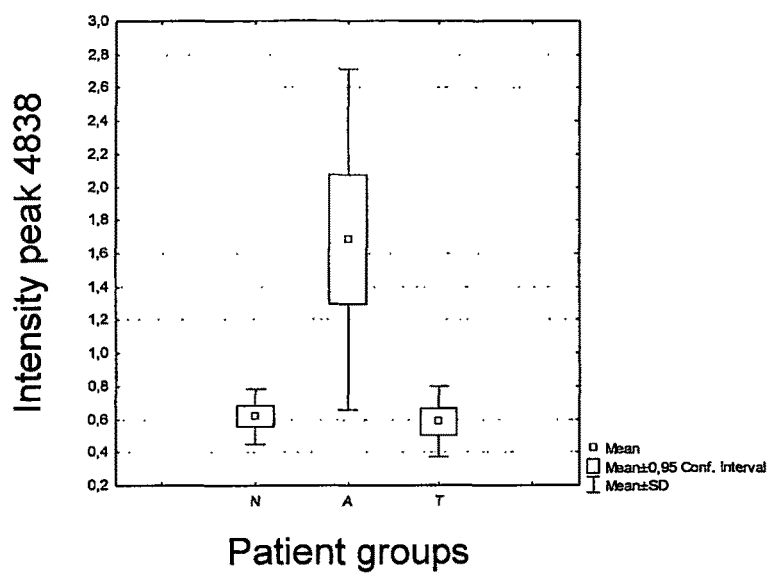

FIG. 9 shows SELDI TOF MS protein profiles of lysates from normal colon, adenoma and cancer tissue. The peak intensity of p4838 (p4.8) is significantly elevated in tissues of colorectal adenoma patients compared to healthy control and colorectal cancer tissues. N=normal tissue, A=adenoma tissue, T=cancer tissue.

FIG. 10 shows that the combination of two markers (p10.3 and p4.8 or p10.3 and p3.4) improved in a heterogenous patient population both, the sensitivity and specificity for adenoma and cancer tissues. A) A sensitivity of 90% for cancer tissue (79% for adenoma) and a specificity of 90% were achieved, if the detection was based on a combination of p 10.3 and p4.8. B) Using the combination of p10.3 and the alpha defensin family member p3.4 the according numbers were 70% for cancer samples (82% for adenoma) with a specificity of 90%. N=normal colon mucosa, T=carcinoma tissue, A=adenoma tissue. The numbers in front of the letter designate the number of separated individuals. The other numbers refer to the Cut-off values.

EXAMPLES

Unless otherwise stated all methods were carried out following the protocol of the manufacturer of the analytical systems.

Example 1

Sample Preparation

Tissue Samples

Tumor tissue from adenoma and colorectal cancer patients (TNM stage III) as well as matched normal colon tissue from each patient were analyzed. Patients: Ethical guidelines and patient confidentiality have been strictly assured and all patients gave written consent to participate in this study. All patients had comparable preoperative preparations such as fasting time and medication at the time of surgery.

Preparation of Tissue Extracts

Cryostat sections (5 µm) from fresh frozen tumor and normal tissues were stained with hematoxilin/eosin to control the histopathology and the amount of tumor/stroma. Tissue blocks with a tumor content or adenoma content over 50% as well as normal tissues were cut into sections (8×20 µm) and immediately transferred into 500 µl Dulbeccos phosphate buffered saline buffer (137 mM NaCl, 2.7 mM KCl, 6.5 mM $Na_2HPO_4.12H_2O$, 1.5 mM $KH_2PO_4$, pH 7.4). The sections were centrifuged at 13,200 rpm for 10 min at 4° C. The pellets were extracted by a 150 µl lysis buffer (20 mM Tris, 50 mM NaCl, 0.5% Tween pH 7.2, 0.1% Complete® (Roche, Mannheim, Germany) for 10 min on ice. After extensive vortexing the lysates were centrifuged for 10 min at 13,200 rpm. The protein concentrations of the supernatants were measured by BCA assay (BCA Assay, Pierce, Rockford, Ill., USA) and were adjusted for each sample to a concentration of 5 µg/50 µl with lysis-buffer.

Example 2

Ciphergen ProteinChip® array preparation. The protein lysates were analyzed on a strong anionic exchanger array (SAX; Ciphergen Biosystems, Femont, Calif., USA). SAX protein arrays (strong anionic exchanger) were processed in a bioprocessor (Ciphergen Biosystems, Inc). Chips were equilibrated with binding buffer (0.1M Tris/HCl, pH 7.5) for 2×5 min and subsequently incubated with 50 µl protein lysate on each spot. After 45 min the unbound material was removed and the chips were washed 3 times with buffer and 2 times with water. After drying, 2 applications of sinapinic acid (1.0 µl) were added and the chips were analyzed with the Ciphergen Protein ChipReader (model PBSII). To minimize data variability, measurement was performed within two days using samples from all patient groups randomly distributed on the chips. As a standard control for normalization, one tissue extract from a cancer patient was used in parallel for all measurements.

SELDI-TOF-MS Analysis.

The mass spectra of proteins were generated by using an average of 195 laser shots at a laser intensity of 180. The detector was run at a sensitivity of 6. For data aquisition, the detection size range was between 2,000 and 40,000 Da. The laser was focused at 10,000 Da. The data were analyzed with the ProteinChip Data Analysis Program (version 3.1, Ciphergen Biosystems) and with the Biomarker Wizard Program (version 3.1, Ciphergen Biosystems). The peak intensities were normalized to the total ion current.

Example 3

Statistical Evaluation of the Data

For the three patient groups cut-off values are calculated by the C&RT(CART) algorithmus on the basis of decision-tree analysis (Breiman, L., Friedman, J. H., Olshen, R. A., & Stone, C. J. (1984). *Classification and regression trees*. Monterey, CA: Wadsworth & Brooks/Cole Advanced Books & Software). The Cutoff-values have been calculated in order to select and specify the limiting values between the different analysis groups. The evaluation has been performed with STATISTICA Software Vs 7.1 from STATSOFT INC, the decision-tree analysis is performed with Data-Miner Modul subprogram Standard Classification Trees (CAndRT) (StatSoft, Inc. (2005). STATISTICA (data analysis software system), version 7.1. www.statsoft.com.)

discriminated from the tumor and normal patient samples with a sensitivity of 76% and a specificity of 100%.

Table 1 summarizes the detected peak intensities in the patient groups for peaks 10,324, 4,838 and the defensin family member peaks 3,375, 3,445 and 3,489.

TABLE 1

| Variable (m/z) | Valid n N | Valid n A | Valid n T | Valid n A + T | Mean ± Std. Dev. N | Mean ± Std. Dev. A | Mean ± Std. Dev. T |
|---|---|---|---|---|---|---|---|
| 3375 | 29 | 29 | 30 | 59 | 3.155 ± 3.476 | 6.54 ± 4.73 | 20.98 ± 12.89 |
| 3445 | 29 | 29 | 30 | 59 | 2.66 ± 3.28 | 5.86 ± 5.1 | 19.79 ± 13.26 |
| 3489 | 29 | 29 | 30 | 59 | 1.14 ± 1.06 | 2.39 ± 2.32 | 14.96 ± 13.39 |
| 4838 | 29 | 29 | 30 | 59 | 0.619 ± 0.166 | 1.68 ± 1.026 | 0.58 ± 0.21 |
| 10324 | 29 | 29 | 30 | 59 | 0.95 ± 0.38 | 2.37 ± 1.24 | 3.44 ± 1.57 |

| Variable (m/z) | Mean ± Std. Dev. A + T | p-Value N vs. A | p-Value N vs. T | p-Value N vs. A + T | p-Value A vs. T |
|---|---|---|---|---|---|
| 3375 | 13.88 ± 12.4 | 0.0029 | 0.0000001 | 0.000011 | 0.0000001 |
| 3445 | 12.85 ± 12.3 | 0.01 | 0.0000001 | 0.000034 | 0.000002 |
| 3489 | 8.78 ± 11.5 | 0.01 | 0.000001 | 0.00061 | 0.000006 |
| 4838 | 1.12 ± 0.91 | 0.000001 | 0.49 | 0.0040 | 0.0000001 |
| 10324 | 2.91 ± 1.5 | 0.0000001 | 0.0000001 | 0.0000001 | 0.00531 | n: number of patients
N: normal tissue
A: adenoma tissue
T: cancer tissue

Figure 6:
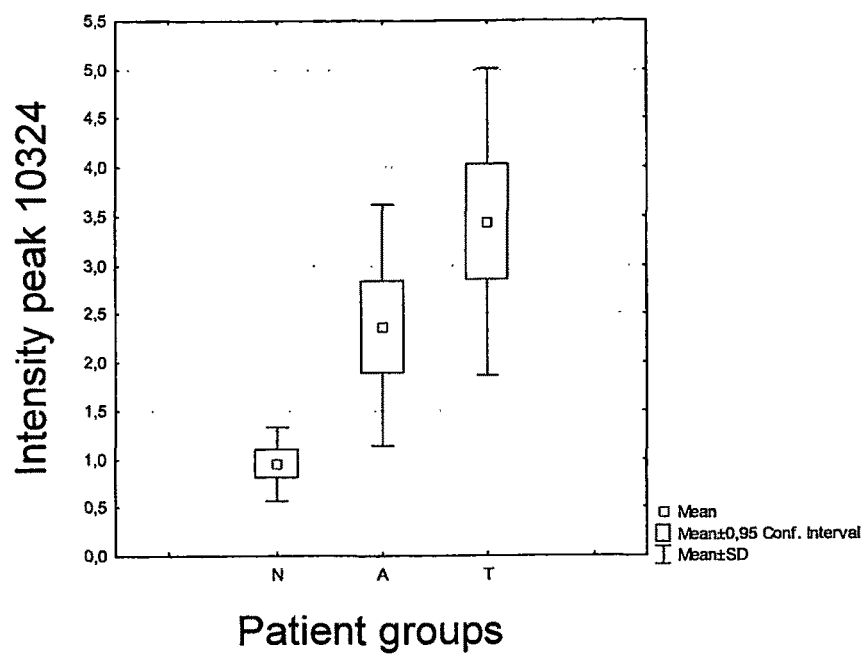
FIG. 6 shows the analysis of endoplasmin fragment p10.3 by SELDI-TOF-MS. 30 samples from colon cancer and 29 samples from adenoma tissue as well as corresponding normal healthy colon tissue were analysed. The mean concentrations of the endoplasmin fragment p10.3 are significantly higher in the adenoma group (A) and/or carcinoma group (T) compared to the healthy group (N).

The statistical data are evaluated on the basis on the mean value and standard deviation. Further, the FIGS. 6, 8 and 9 show a confidence interval of mean±0.95, indicating to find the true mean values of the prospect patient groups with 95% probability within this interval. The statistical evaluation is performed by the T-Test (Table 1). The tests were considered to be significant with p-levels <0.05. The whiskers of the box plots show the standard deviation.

Example 4

Figure 4:
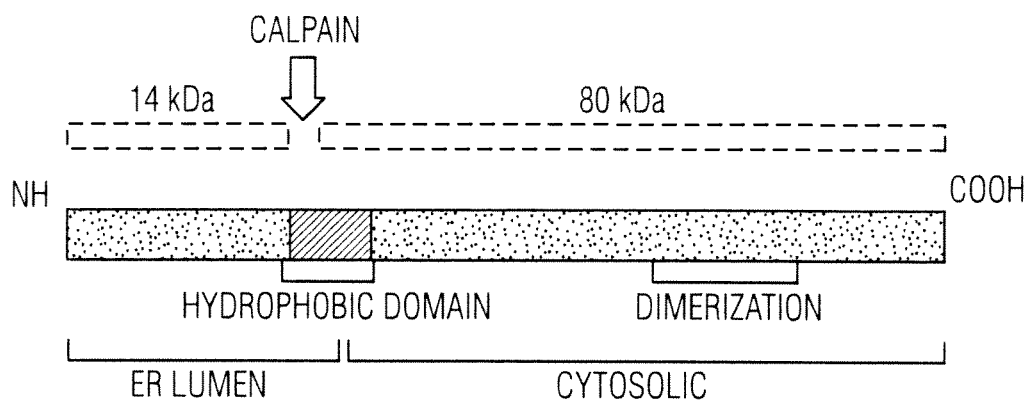
FIG. 4 shows the putative cleavage site of endoplasmin by calpain to generate an about 80 kDa and an about 14 kDa fragment.
Figure 5:
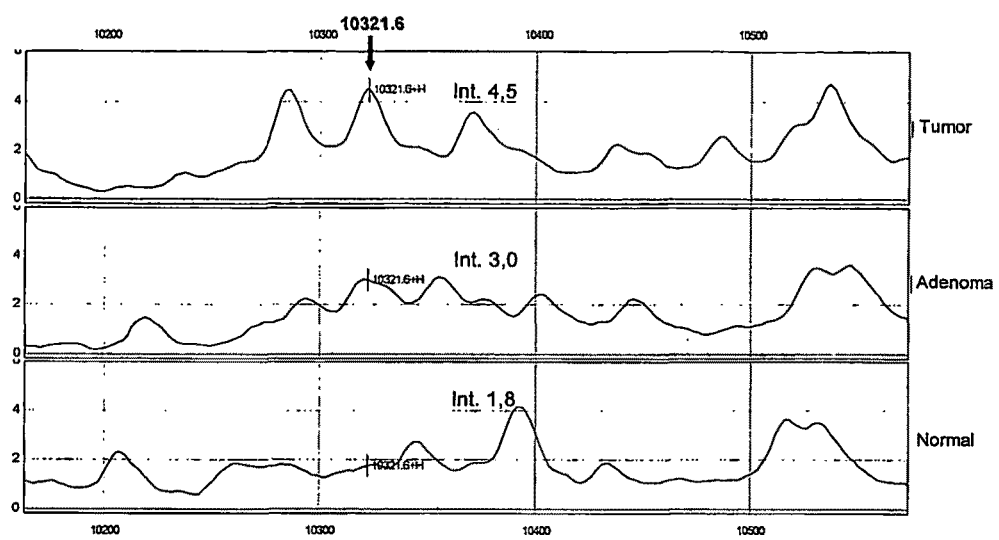
FIG. 5 shows SELDI-TOF-MS protein profiles of lysates from normal colon, adenoma and tumor tissue. The intensity of p10.3 (N-terminal part of endoplasmin, 10,300 Da) increases significantly in tissue from healthy to adenoma to cancer patients.

Protein samples of tumor tissue from one adenoma and one colorectal cancer patient (TNM stage II) as well as normal colon tissue has been prepared and analysed according to Examples 1 and 2. FIG. 5 shows SELDI-TOF protein profiles of lysates from normal colon, adenoma and tumor tissue. The intensity of p10.3 increases significantly in tissue from healthy to cancer patients.

FIG. 6 shows the mean intensities of p10.3 (endoplasmin fragment) in normal, adenoma and colon cancer tissue. 30 colon cancer and 29 adenoma tissue samples as well as corresponding normal colon tissue were analysed according to examples 1 to 3. Differences in mean intensities of p10.3 in normal and colon tumor tissue as well as in normal and adenoma tissue were statistically significant. For the discrimination of tumor samples a specificity of 97% and sensitivity of 93% was achieved. The specificity for adenoma samples was 90% with a sensitivity of 86%.

FIG. 8 shows the mean intensities of one of the identified alpha-defensin family members (peak 3,489) in the same patient population. The mean intensities in the adenoma and colon cancer groups were significantly elevated compared to normal colon tissue levels. A discrimination of adenoma samples was achieved with a sensitivity of 52% and a specificity of 90%. The respective values for discrimination of tumor samples were 90% and 89.6%.

FIG. 9 shows the specifically elevated level of peak 4838 in the adenoma group samples. The adenoma samples could be All data in Table 1 were obtained by SELDI-TOF-MS Example 5

Expression of p10.3 in Different Tissues

In order to identify p10.3 as colon-specific biomarker cell extracts were prepared and analysed by mass spectroscopy according to Examples 1 and 2 for different tumor tissue namely breast, stomach, esophagus, lung and prostate. As shown in FIG. 7 and Table 2 the highest intensity of p 10.3 can be found in colorectal carcinoma. (stadium I and III). However, the endoplasmin fragment is expressed at a lower level in esophagus, lung and prostate cancer and normal tissue.

TABLE 2

Intensities of p 10.3 in different cancer types. The lysates were analysed on a SAX Protein Chip ®Array.

| Tissue type | | Intensity p10.3 |
|---|---|---|
| Breast | normal | 1.002 |
| | tumor | 0.672 |
| Lung | normal | 1.431 |
| | tumor | 1.907 |
| Stomach | normal | 1.849 |
| | tumor | 1.629 |
| Esophagus | normal | 0.506 |
| | tumor | 0.944 |
| Prostate | normal | 0.933 |
| | tumor | 0.852 |
| Colon (stadium I) | normal | 0.948 |
| | tumor | 2.830 |
| Colon (stadium III) | normal | 1.035 |
| | tumor | 3.283 |

It can be seen from FIG. 7 that endoplasmin fragments, especially the protein fragment having an apparent molecular weight of 10,300 Da (p10.3), are highly specific for colon carcinoma. In contrast to tumor of breast, lung, stomach, esophagus or prostate, there is a significant difference in the level of p10.3 between healthy and diseased patients. Moreover, the level of p10.3 increases with the cancer stage (stadium I versus stadium III).

Example 6

30 colon cancer and 29 adenoma tissue samples as well as corresponding normal colon tissue were isolated and analysed as described in Examples 1 to 3 except that a second marker, a protein either having a molecular weight of 4,838 Da (p4.8) or a molecular weight of 3,489 Da (p3.4), has been used in combination with the endoplasmin fragment peak. In combination with a second marker protein, e.g. 4,838 Da (p4.8) or 3,489 Da (p3.4), simultaneous separation of normal tissue from adenoma and/or cancer tissues was achieved. Using p10.3 as first and p4.8 as second marker, 26 out of 29 (specificity 90%) normal tissue samples, 23 of 29 adenoma samples (sensitivity 79%) as well as 27 of 30 cancer samples (sensitivity 90%) were correctly separated (FIG. 10A). The combination with peak 3489 achieved a specificity of 90% and a sensitivity of 82% for adenoma samples and 70% for tumor samples (FIG. 10B).

Results

As shown in FIG. 6 the amount of the endoplasmin fragment differs significantly between the three groups (N=normal A=adenoma T=cancer). The endoplasmin fragment level increases from healthy individuals over colorectal adenoma patients to colorectal carcinoma patients.

These data show that an endoplasmin fragment, optionally in combination with other biomarkers such as a protein having a molecular weight of 4,838 Da (p4.8) or of 3,489 Da (p3.4), is (are) an excellent biomarker(s) for the detection of colorectal adenoma and/or colorectal carcinoma.

In contrast to already known biomarkers CEA and CA 19-9 it is possible to discriminate between healthy individuals and adenoma patients. Furthermore, it is possible to discriminate adenoma patients and colorectal carcinoma patients. The sensitivity and specificity of the endoplasmin fragment test is high and allows an early specific detection of adenomas as well as the discrimination between different tumor stages.

The invention claimed is:

1. A method for detecting colorectal adenoma and/or colorectal carcinoma comprising the steps:
    (a) providing an isolated colorectal tissue sample which has been taken from an individual,
    (b) determining the level of an endoplasmin fragment in said isolated sample,
    (c) comparing the determined level of an endoplasmin fragment with one or more reference values,
    wherein the endoplasmin fragment has a molecular weight of 10.3 kDa, and wherein the level of said endoplasmin fragment in said colorectal tissue sample taken from a colorectal adenoma or colorectal carcinoma patient is increased compared to a colorectal sample from a healthy individual, whereby colorectal adenoma and/or colorectal carcinoma is detected.

2. The method of claim 1, wherein the endoplasmin fragment comprises the peptide sequence SEQ ID NO: 2 and/or SEQ ID NO: 3 or SEQ ID NO: 4.

3. The method of claim 1, wherein a first increase of the level of said endoplasmin fragment in a first colorectal tissue sample is indicative for colorectal adenoma and wherein a second increase of the level of said endoplasmin fragment in a second colorectal tissue sample, isolated from said individual at a later point in time than said first colorectal tissue sample, is indicative for colorectal carcinoma, with the proviso that said second increase is greater than said first increase.

4. The method of claim 1, wherein in step (b) one or more further biomarker(s) for detecting colorectal adenoma and/or colorectal carcinoma is/are determined in said isolated colorectal tissue sample and wherein in step (c) the determined level of said biomarker(s) is/are compared with one or more respective reference values.

5. The method of claim 4, wherein said further biomarker (s) for detecting colorectal adenoma and/or colorectal carcinoma is/are selected from the group selected from the group consisting of alpha-defensin 1, 2 or 3, transthyretin, p53, C3a, CEA (carcinoembryonic antigen), CA 19-9, CA 15-3, CA-125, Kras, β-Catenin, Her-2/neu, C-reactive protein, and mutations in E-cadherin, MSH2, MSH3, MLH1, PMS1, PMS2, MSH6 genes, and microsatellite instability of MHL1 or MSH2, and combinations thereof.

6. The method of claim 4, wherein the reference value(s) of said endoplasmin fragment and optionally the reference value (s) of the further biomarker(s) is/are calculated as the average level of said endoplasmin fragment and optionally further biomarker(s) in a plurality of isolated colorectal tissue samples of a respective group of individuals, wherein the group of individuals are healthy individuals, colorectal adenoma patients, and/or colorectal carcinoma patients.

7. The method of claim 4, wherein the reference value is an individual reference value calculated as the average level of said endoplasmin fragment and optionally of further biomarker(s) determined in a plurality of isolated colorectal tissue samples taken from said individual over a period of time.

8. The method of claim 4, wherein the level of said endoplasmin fragment and optionally of further biomarker(s) in said colorectal tissue sample is(are) determined by immunological methods or proteomics technique and/or mass spectroscopy.

9. The method of claim 1, wherein the said method is carried out in combination with at least one other diagnostic method for colorectal adenoma and/or colorectal carcinoma to increase sensitivity and/or specificity.

10. A method for determining whether a compound is effective in the treatment of colorectal adenoma and/or colorectal carcinoma and/or specific colorectal tumor stages comprising the steps:
(a) treating a colorectal adenoma or colorectal carcinoma patient with a compound,
(b) determining the level of an endoplasmin fragment in a colorectal tissue sample of said patient, and
(c) comparing the determined level of an endoplasmin fragment with one or more reference values,
wherein said endoplasmin fragment has a molecular weight of 10.3 kDa, and wherein the level of said endoplasmin fragment in said colorectal tissue sample taken from a colorectal adenoma or colorectal carcinoma patient is increased compared to a colorectal sample from a healthy individual, whereby the level of said endoplasmin fragment indicates whether said compound is effective in the treatment of colorectal adenoma and/or colorectal carcinoma and/or specific colorectal tumor stages.

11. The method according to claim 10, wherein in step (b) one or more further biomarker(s) for detecting colorectal adenoma and/or colorectal carcinoma and/or discrimination of different colorectal tumor stages is/are determined in said isolated colorectal tissue sample and wherein in step (c) the determined level of said biomarker(s) is/are compared with one or more respective reference values.

12. The method according to claim 11, wherein said at least one further biomarker is selected from the group consisting of alpha-defensin 1, 2 or 3, transthyretin, p53, C3a, CEA (carcinoembryonic antigen), CA 19-9, CA 15-3, CA-125, Kras, β-Catenin, Her-2/neu, C-reactive protein, and mutations in E-cadherin, MSH2, MSH3, MLH1, PMS1, PMS2, MSH6 genes, and microsatellite instability of MHL1 or MSH2, and combinations thereof.

13. A method for discriminating between colorectal adenoma and colorectal carcinoma comprising the steps:
(a) providing an isolated colorectal tissue sample which has been taken from an individual,
(b) determining the level of an endoplasmin fragment in said isolated colorectal tissue sample,
(c) comparing the determined level of an endoplasmin fragment with one or more reference values,
wherein the endoplasmin fragment has a molecular weight of 10.3 kDa, and wherein the level of said endoplasmin fragment in said colorectal tissue sample taken from a colorectal adenoma or colorectal carcinoma patient is increased compared to a colorectal tissue sample from a healthy individual, whereby said level of said endoplasmin fragment discriminates between colorectal adenoma and colorectal carcinoma.

14. The method of claim 13, wherein the endoplasmin fragment comprises the peptide sequence SEQ ID NO: 2 and/or SEQ ID NO: 3 or SEQ ID NO: 4.

15. The method of claim 13, wherein a first increase of the level of said endoplasmin fragment in a first colorectal tissue sample is indicative for colorectal adenoma and wherein a second increase of the level of an endoplasmin fragment in a second colorectal tissue sample, isolated from said individual at a later point in time than said first colorectal tissue sample, is indicative for colorectal carcinoma, with the proviso that said second increase is greater than said first increase.

16. The method of claim 13, wherein in step (b) one or more further biomarker(s) for detecting colorectal adenoma and/or colorectal carcinoma is/are determined in said isolated colorectal tissue sample and wherein in step (c) the determined level of said biomarker(s) is/are compared with one or more respective reference values.

17. The method of claim 16, wherein said further biomarker(s) for detecting colorectal adenoma and/or colorectal carcinoma is/are selected from the group selected from the group consisting of alpha-defensin 1, 2 or 3, transthyretin, p53, C3a, CEA (carcinoembryonic antigen), CA 19-9, CA 15-3, CA-125, Kras, β-Catenin, Her-2/neu, C-reactive protein, and mutations in E-cadherin, MSH2, MSH3, MLH1, PMS1, PMS2, MSH6 genes, and microsatellite instability of MHL1 or MSH2, and combinations thereof.

18. The method of claim 16, wherein the reference value(s) of an said endoplasmin fragment and optionally the reference value(s) of the further biomarker(s) is/are calculated as the average level of said endoplasmin fragment and optionally further biomarker(s) in a plurality of isolated colorectal tissue samples of a respective group of individuals, wherein the group of individuals are healthy individuals, colorectal adenoma patients and/or colorectal carcinoma patients.

19. The method of claim 16, wherein the reference value is an individual reference value calculated as the average level of said endoplasmin fragment and optionally of further biomarker(s) determined in a plurality of isolated colorectal tissue samples taken from said individual over a period of time.

20. The method of claim 16, wherein the level of said endoplasmin fragment and optionally of further biomarker(s) in said colorectal tissue sample is (are) determined by immunological methods or proteomics technique and/or mass spectroscopy.

21. The method of claim 13, wherein the method is carried out in combination with at least one other diagnostic method for colorectal adenoma and/or colorectal carcinoma to increase sensitivity and/or specificity.

22. A method for monitoring the development and/or course and/or the treatment of colorectal adenoma and/or colorectal carcinoma and/or for discrimination between different colorectal tumor stages comprising the steps:
(a) providing an isolated colorectal tissue sample which has been taken from an individual,
(b) determining the level of an endoplasmin fragment in said isolated sample,
(c) comparing the determined level of an endoplasmin fragment with one or more reference values,
wherein the endoplasmin fragment has a molecular weight of 10.3 kDa, and wherein the level of said endoplasmin fragment in said colorectal tissue sample taken from a colorectal adenoma or colorectal carcinoma patient is increased compared to a colorectal tissue sample of a healthy individual, whereby said level of said endoplasmin fragment monitors the development and/or course and/or the treatment of colorectal adenoma and/or colorectal carcinoma and/or discriminates between different colorectal tumor stages.

23. The method of claim 22, wherein the endoplasmin fragment comprises the peptide sequence SEQ ID NO: 2 and/or SEQ ID NO: 3 or SEQ ID NO: 4.

24. The method of claim 22, wherein a first increase of the level of said endoplasmin fragment in a first colorectal tissue sample is indicative for colorectal adenoma and wherein a second increase of the level of an endoplasmin fragment in a second colorectal tissue sample isolated from said individual at a later point in time than said first colorectal tissue sample, is indicative for colorectal carcinoma, with the proviso that said second increase is greater than said first increase.

25. The method of claim 22, wherein in step (b) one or more further biomarker(s) for detecting colorectal adenoma and/or colorectal carcinoma is/are determined in said isolated colorectal tissue sample and wherein in step (c) the determined level of said biomarker(s) is/are compared with one or more respective reference values.

26. The method of claim 25, wherein said further biomarker(s) for detecting colorectal adenoma and/or colorectal carcinoma is/are selected from the group selected from the group consisting of alpha-defensin 1, 2 or 3, transthyretin, p53, C3a, CEA (carcinoembryonic antigen), CA 19-9, CA 15-3, CA-125, Kras, β-Catenin, Her-2/neu, C-reactive protein, and mutations in E-cadherin, MSH2, MSH3, MLH1, PMS1, PMS2, MSH6 genes, and microsatellite instability of MHL1 or MSH2, and combinations thereof.

27. The method of claim 25, wherein the reference value(s) of said endoplasmin fragment and optionally the reference value(s) of the further biomarker(s) is/are calculated as the average level of said endoplasmin fragment and optionally further biomarker(s) in a plurality of isolated colorectal tissue samples of a respective group of individuals, wherein the group of individuals are healthy individuals, colorectal adenoma patients and/or colorectal carcinoma patients.

28. The method of claim 25, wherein the reference value is an individual reference value calculated as the average level of said endoplasmin fragment and optionally of further biomarker(s) determined in a plurality of isolated colorectal tissue samples taken from said individual over a period of time.

29. The method of claim 25, wherein the level of said endoplasmin fragment and optionally of further biomarker(s) in said colorectal tissue sample is (are) determined by immunological methods, proteomics technique and/or mass spectroscopy.

30. The method of claim 25, wherein the method is carried out in combination with other diagnostic methods for colorectal adenoma and/or colorectal carcinoma to increase sensitivity and/or specificity.

* * * * *

SEQUENCE LISTING

<160> NUMBER OF SEQ ID NOS: 7

<210> SEQ ID NO 1
<211> LENGTH: 803
<212> TYPE: PRT
<213> ORGANISM: human

<400> SEQUENCE: 1

```
Met Arg Ala Leu Trp Val Leu Gly Leu Cys Cys Val Leu Leu Thr Phe
1               5                   10                  15

Gly Ser Val Arg Ala Asp Asp Glu Val Asp Val Asp Gly Thr Val Glu
            20                  25                  30

Glu Asp Leu Gly Lys Ser Arg Glu Gly Ser Arg Thr Asp Asp Glu Val
        35                  40                  45

Val Gln Arg Glu Glu Glu Ala Ile Gln Leu Asp Gly Leu Asn Ala Ser
    50                  55                  60

Gln Ile Arg Glu Leu Arg Glu Lys Ser Glu Lys Phe Ala Phe Gln Ala
65                  70                  75                  80

Glu Val Asn Arg Met Met Lys Leu Ile Ile Asn Ser Leu Tyr Lys Asn
                85                  90                  95

Lys Glu Ile Phe Leu Arg Glu Leu Ile Ser Asn Ala Ser Asp Ala Leu
            100                 105                 110

Asp Lys Ile Arg Leu Ile Ser Leu Thr Asp Glu Asn Ala Leu Ser Gly
        115                 120                 125

Asn Glu Glu Leu Thr Val Lys Ile Lys Cys Asp Lys Glu Lys Asn Leu
    130                 135                 140

Leu His Val Thr Asp Thr Gly Val Gly Met Thr Arg Glu Glu Leu Val
145                 150                 155                 160

Lys Asn Leu Gly Thr Ile Ala Lys Ser Gly Thr Ser Glu Phe Leu Asn
                165                 170                 175

Lys Met Thr Glu Ala Gln Glu Asp Gly Gln Ser Thr Ser Glu Leu Ile
            180                 185                 190

Gly Gln Phe Gly Val Gly Phe Tyr Ser Ala Phe Leu Val Ala Asp Lys
        195                 200                 205

Val Ile Val Thr Ser Lys His Asn Asn Asp Thr Gln His Ile Trp Glu
    210                 215                 220
```

```
Ser Asp Ser Asn Glu Phe Ser Val Ile Ala Asp Pro Arg Gly Asn Thr
225                 230                 235                 240

Leu Gly Arg Gly Thr Thr Ile Thr Leu Val Leu Lys Glu Glu Ala Ser
            245                 250                 255

Asp Tyr Leu Glu Leu Asp Thr Ile Lys Asn Leu Val Lys Lys Tyr Ser
        260                 265                 270

Gln Phe Ile Asn Phe Pro Ile Tyr Val Trp Ser Ser Lys Thr Glu Thr
    275                 280                 285

Val Glu Glu Pro Met Glu Glu Glu Ala Ala Lys Glu Glu Lys Glu
290                 295                 300

Glu Ser Asp Asp Glu Ala Ala Val Glu Glu Glu Glu Glu Lys Lys
305                 310                 315                 320

Pro Lys Thr Lys Lys Val Glu Lys Thr Val Trp Asp Trp Glu Leu Met
            325                 330                 335

Asn Asp Ile Lys Pro Ile Trp Gln Arg Pro Ser Lys Glu Val Glu Glu
                340                 345                 350

Asp Glu Tyr Lys Ala Phe Tyr Lys Ser Phe Ser Lys Glu Ser Asp Asp
        355                 360                 365

Pro Met Ala Tyr Ile His Phe Thr Ala Glu Gly Glu Val Thr Phe Lys
370                 375                 380

Ser Ile Leu Phe Val Pro Thr Ser Ala Pro Arg Gly Leu Phe Asp Glu
385                 390                 395                 400

Tyr Gly Ser Lys Lys Ser Asp Tyr Ile Lys Leu Tyr Val Arg Arg Val
                405                 410                 415

Phe Ile Thr Asp Asp Phe His Asp Met Met Pro Lys Tyr Leu Asn Phe
                420                 425                 430

Val Lys Gly Val Val Asp Ser Asp Asp Leu Pro Leu Asn Val Ser Arg
            435                 440                 445

Glu Thr Leu Gln Gln His Lys Leu Leu Lys Val Ile Arg Lys Lys Leu
        450                 455                 460

Val Arg Lys Thr Leu Asp Met Ile Lys Lys Ile Ala Asp Asp Lys Tyr
465                 470                 475                 480

Asn Asp Thr Phe Trp Lys Glu Phe Gly Thr Asn Ile Lys Leu Gly Val
                485                 490                 495

Ile Glu Asp His Ser Asn Arg Thr Arg Leu Ala Lys Leu Leu Arg Phe
                500                 505                 510

Gln Ser Ser His His Pro Thr Asp Ile Thr Ser Leu Asp Gln Tyr Val
        515                 520                 525

Glu Arg Met Lys Glu Lys Gln Asp Lys Ile Tyr Phe Met Ala Gly Ser
        530                 535                 540

Ser Arg Lys Glu Ala Glu Ser Ser Pro Phe Val Glu Arg Leu Leu Lys
545                 550                 555                 560

Lys Gly Tyr Glu Val Ile Tyr Leu Thr Glu Pro Val Asp Glu Tyr Cys
            565                 570                 575

Ile Gln Ala Leu Pro Glu Phe Asp Gly Lys Arg Phe Gln Asn Val Ala
                580                 585                 590

Lys Glu Gly Val Lys Phe Asp Glu Ser Glu Lys Thr Lys Glu Ser Arg
            595                 600                 605

Glu Ala Val Glu Lys Glu Phe Glu Pro Leu Leu Asn Trp Met Lys Asp
        610                 615                 620

Lys Ala Leu Lys Asp Lys Ile Glu Lys Ala Val Val Ser Gln Arg Leu
625                 630                 635                 640

Thr Glu Ser Pro Cys Ala Leu Val Ala Ser Gln Tyr Gly Trp Ser Gly
                645                 650                 655
```

Asn Met Glu Arg Ile Met Lys Ala Gln Ala Tyr Gln Thr Gly Lys Asp
                660                 665                 670

Ile Ser Thr Asn Tyr Tyr Ala Ser Gln Lys Lys Thr Phe Glu Ile Asn
            675                 680                 685

Pro Arg His Pro Leu Ile Arg Asp Met Leu Arg Arg Ile Lys Glu Asp
690                 695                 700

Glu Asp Asp Lys Thr Val Leu Asp Leu Ala Val Val Leu Phe Glu Thr
705                 710                 715                 720

Ala Thr Leu Arg Ser Gly Tyr Leu Leu Pro Asp Thr Lys Ala Tyr Gly
                725                 730                 735

Asp Arg Ile Glu Arg Met Leu Arg Leu Ser Leu Asn Ile Asp Pro Asp
            740                 745                 750

Ala Lys Val Glu Glu Pro Glu Glu Pro Glu Glu Thr Ala Glu
            755                 760                 765

Asp Thr Thr Glu Asp Thr Glu Gln Asp Glu Asp Glu Met Asp Val
            770                 775                 780

Gly Thr Asp Glu Glu Glu Glu Thr Ala Lys Glu Ser Thr Ala Glu Lys
785                 790                 795                 800

Asp Glu Leu

<210> SEQ ID NO 2
<211> LENGTH: 16
<212> TYPE: PRT
<213> ORGANISM: human

<400> SEQUENCE: 2

Glu Glu Glu Ala Ile Gln Leu Asp Gly Leu Asn Ala Ser Gln Ile Arg
1               5                   10                  15

<210> SEQ ID NO 3
<211> LENGTH: 9
<212> TYPE: PRT
<213> ORGANISM: human

<400> SEQUENCE: 3

Phe Ala Phe Gln Ala Glu Val Asn Arg
1               5

<210> SEQ ID NO 4
<211> LENGTH: 33
<212> TYPE: PRT
<213> ORGANISM: human

<400> SEQUENCE: 4

Glu Glu Glu Ala Ile Gln Leu Asp Gly Leu Asn Ala Ser Gln Ile Arg
1               5                   10                  15

Glu Leu Arg Glu Lys Ser Glu Lys Phe Ala Phe Gln Ala Glu Val Asn
                20                  25                  30

Arg

<210> SEQ ID NO 5
<211> LENGTH: 1641
<212> TYPE: PRT
<213> ORGANISM: human

<400> SEQUENCE: 5

Ser Pro Met Tyr Ser Ile Ile Thr Pro Asn Ile Leu Arg Leu Glu Ser
1               5                   10                  15

Glu Glu Thr Met Val Leu Glu Ala His Asp Ala Gln Gly Asp Val Pro

```
                    20                  25                  30
Val Thr Val Thr Val His Asp Phe Pro Gly Lys Lys Leu Val Leu Ser
                35                  40                  45

Ser Glu Lys Thr Val Leu Thr Pro Ala Thr Asn His Met Gly Asn Val
            50                  55                  60

Thr Phe Thr Ile Pro Ala Asn Arg Glu Phe Lys Ser Glu Lys Gly Arg
65                  70                  75                  80

Asn Lys Phe Val Thr Val Gln Ala Thr Phe Gly Thr Gln Val Val Glu
                85                  90                  95

Lys Val Val Leu Val Ser Leu Gln Ser Gly Tyr Leu Phe Ile Gln Thr
                100                 105                 110

Asp Lys Thr Ile Tyr Thr Pro Gly Ser Thr Val Leu Tyr Arg Ile Phe
            115                 120                 125

Thr Val Asn His Lys Leu Leu Pro Val Gly Arg Thr Val Met Val Asn
        130                 135                 140

Ile Glu Asn Pro Glu Gly Ile Pro Val Lys Gln Asp Ser Leu Ser Ser
145                 150                 155                 160

Gln Asn Gln Leu Gly Val Leu Pro Leu Ser Trp Asp Ile Pro Glu Leu
                165                 170                 175

Val Asn Met Gly Gln Trp Lys Ile Arg Ala Tyr Tyr Glu Asn Ser Pro
                180                 185                 190

Gln Gln Val Phe Ser Thr Glu Phe Glu Val Lys Glu Tyr Val Leu Pro
                195                 200                 205

Ser Phe Glu Val Ile Val Glu Pro Thr Glu Lys Phe Tyr Tyr Ile Tyr
            210                 215                 220

Asn Glu Lys Gly Leu Glu Val Thr Ile Thr Ala Arg Phe Leu Tyr Gly
225                 230                 235                 240

Lys Lys Val Glu Gly Thr Ala Phe Val Ile Phe Gly Ile Gln Asp Gly
                245                 250                 255

Glu Gln Arg Ile Ser Leu Pro Gly Ser Leu Lys Arg Ile Pro Ile Glu
            260                 265                 270

Asp Gly Ser Gly Glu Val Val Leu Ser Arg Lys Val Leu Leu Asp Gly
        275                 280                 285

Val Gln Asn Leu Arg Ala Glu Asp Leu Val Gly Lys Ser Leu Tyr Val
        290                 295                 300

Ser Ala Thr Val Ile Leu His Ser Gly Ser Asp Met Val Gln Ala Glu
305                 310                 315                 320

Arg Ser Gly Ile Pro Ile Val Thr Ser Pro Tyr Gln Ile His Phe Thr
            325                 330                 335

Lys Thr Pro Lys Tyr Phe Lys Pro Gly Met Pro Phe Asp Leu Met Val
            340                 345                 350

Phe Val Thr Asn Pro Asp Gly Ser Pro Ala Tyr Arg Val Pro Val Ala
                355                 360                 365

Val Gln Gly Glu Asp Thr Val Gln Ser Leu Thr Gln Gly Asp Gly Val
            370                 375                 380

Ala Lys Leu Ser Ile Asn Thr His Pro Ser Gln Lys Pro Leu Ser Ile
385                 390                 395                 400

Thr Val Arg Thr Lys Lys Gln Glu Leu Ser Glu Ala Glu Gln Ala Thr
                405                 410                 415

Arg Thr Met Gln Ala Leu Pro Tyr Ser Thr Val Gly Asn Ser Asn Asn
                420                 425                 430

Tyr Leu His Leu Ser Val Leu Arg Thr Glu Leu Arg Pro Gly Glu Thr
            435                 440                 445
```

-continued

```
Leu Asn Val Asn Phe Leu Leu Arg Met Asp Arg Ala His Glu Ala Lys
450                 455                 460
Ile Arg Tyr Tyr Thr Tyr Leu Ile Met Asn Lys Gly Arg Leu Leu Lys
465                 470                 475                 480
Ala Gly Arg Gln Val Arg Glu Pro Gly Gln Asp Leu Val Val Leu Pro
                485                 490                 495
Leu Ser Ile Thr Thr Asp Phe Ile Pro Ser Phe Arg Leu Val Ala Tyr
                500                 505                 510
Tyr Thr Leu Ile Gly Ala Ser Gly Gln Arg Glu Val Ala Asp Ser
                515                 520                 525
Val Trp Val Asp Val Lys Asp Ser Cys Val Gly Ser Leu Val Val Lys
530                 535                 540
Ser Gly Gln Ser Glu Asp Arg Gln Pro Val Pro Gly Gln Gln Met Thr
545                 550                 555                 560
Leu Lys Ile Glu Gly Asp His Gly Ala Arg Val Val Leu Val Ala Val
                565                 570                 575
Asp Lys Gly Val Phe Val Leu Asn Lys Lys Asn Lys Leu Thr Gln Ser
                580                 585                 590
Lys Ile Trp Asp Val Val Glu Lys Ala Asp Ile Gly Cys Thr Pro Gly
                595                 600                 605
Ser Gly Lys Asp Tyr Ala Gly Val Phe Ser Asp Ala Gly Leu Thr Phe
                610                 615                 620
Thr Ser Ser Ser Gly Gln Gln Thr Ala Gln Arg Ala Glu Leu Gln Cys
625                 630                 635                 640
Pro Gln Pro Ala Ala Arg Arg Arg Ser Val Gln Leu Thr Glu Lys
                645                 650                 655
Arg Met Asp Lys Val Gly Lys Tyr Pro Lys Glu Leu Arg Lys Cys Cys
                660                 665                 670
Glu Asp Gly Met Arg Glu Asn Pro Met Arg Phe Ser Cys Gln Arg Arg
                675                 680                 685
Thr Arg Phe Ile Ser Leu Gly Glu Ala Cys Lys Lys Val Phe Leu Asp
690                 695                 700
Cys Cys Asn Tyr Ile Thr Glu Leu Arg Arg Gln His Ala Arg Ala Ser
705                 710                 715                 720
His Leu Gly Leu Ala Arg Ser Asn Leu Asp Glu Asp Ile Ile Ala Glu
                725                 730                 735
Glu Asn Ile Val Ser Arg Ser Glu Phe Pro Glu Ser Trp Leu Trp Asn
                740                 745                 750
Val Glu Asp Leu Lys Glu Pro Pro Lys Asn Gly Ile Ser Thr Lys Leu
                755                 760                 765
Met Asn Ile Phe Leu Lys Asp Ser Ile Thr Thr Trp Glu Ile Leu Ala
770                 775                 780
Val Ser Met Ser Asp Lys Lys Gly Ile Cys Val Ala Asp Pro Phe Glu
785                 790                 795                 800
Val Thr Val Met Gln Asp Phe Ile Asp Leu Arg Leu Pro Tyr Ser
                805                 810                 815
Val Val Arg Asn Glu Gln Val Glu Ile Arg Ala Val Leu Tyr Asn Tyr
                820                 825                 830
Arg Gln Asn Gln Glu Leu Lys Val Arg Val Glu Leu Leu His Asn Pro
                835                 840                 845
Ala Phe Cys Ser Leu Ala Thr Thr Lys Arg Arg His Gln Gln Thr Val
850                 855                 860
Thr Ile Pro Pro Lys Ser Ser Leu Ser Val Pro Tyr Val Ile Val Pro
865                 870                 875                 880
```

```
Leu Lys Thr Gly Leu Gln Glu Val Glu Val Lys Ala Ala Val Tyr His
            885                 890                 895
His Phe Ile Ser Asp Gly Val Arg Lys Ser Leu Lys Val Val Pro Glu
            900                 905                 910
Gly Ile Arg Met Asn Lys Thr Val Ala Val Arg Thr Leu Asp Pro Glu
            915                 920                 925
Arg Leu Gly Arg Glu Gly Val Gln Lys Glu Asp Ile Pro Pro Ala Asp
            930                 935                 940
Leu Ser Asp Gln Val Pro Asp Thr Glu Ser Glu Thr Arg Ile Leu Leu
945                 950                 955                 960
Gln Gly Thr Pro Val Ala Gln Met Thr Glu Asp Ala Val Asp Ala Glu
            965                 970                 975
Arg Leu Lys His Leu Ile Val Thr Pro Ser Gly Cys Gly Glu Gln Asn
            980                 985                 990
Met Ile Gly Met Thr Pro Thr Val Ile Ala Val His Tyr Leu Asp Glu
            995                1000                1005
Thr Glu Gln Trp Glu Lys Phe Gly Leu Glu Lys Arg Gln Gly Ala
        1010                1015                1020
Leu Glu Leu Ile Lys Lys Gly Tyr Thr Gln Leu Ala Phe Arg
        1025                1030                1035
Gln Pro Ser Ser Ala Phe Ala Ala Phe Val Lys Arg Ala Pro Ser
        1040                1045                1050
Thr Trp Leu Thr Ala Tyr Val Val Lys Val Phe Ser Leu Ala Val
        1055                1060                1065
Asn Leu Ile Ala Ile Asp Ser Gln Val Leu Cys Gly Ala Val Lys
        1070                1075                1080
Trp Leu Ile Leu Glu Lys Gln Lys Pro Asp Gly Val Phe Gln Glu
        1085                1090                1095
Asp Ala Pro Val Ile His Gln Glu Met Ile Gly Gly Leu Arg Asn
        1100                1105                1110
Asn Asn Glu Lys Asp Met Ala Leu Thr Ala Phe Val Leu Ile Ser
        1115                1120                1125
Leu Gln Glu Ala Lys Asp Ile Cys Glu Glu Gln Val Asn Ser Leu
        1130                1135                1140
Pro Gly Ser Ile Thr Lys Ala Gly Asp Phe Leu Glu Ala Asn Tyr
        1145                1150                1155
Met Asn Leu Gln Arg Ser Tyr Thr Val Ala Ile Ala Gly Tyr Ala
        1160                1165                1170
Leu Ala Gln Met Gly Arg Leu Lys Gly Pro Leu Leu Asn Lys Phe
        1175                1180                1185
Leu Thr Thr Ala Lys Asp Lys Asn Arg Trp Glu Asp Pro Gly Lys
        1190                1195                1200
Gln Leu Tyr Asn Val Glu Ala Thr Ser Tyr Ala Leu Leu Ala Leu
        1205                1210                1215
Leu Gln Leu Lys Asp Phe Asp Phe Val Pro Pro Val Val Arg Trp
        1220                1225                1230
Leu Asn Glu Gln Arg Tyr Tyr Gly Gly Gly Tyr Gly Ser Thr Gln
        1235                1240                1245
Ala Thr Phe Met Val Phe Gln Ala Leu Ala Gln Tyr Gln Lys Asp
        1250                1255                1260
Ala Pro Asp His Gln Glu Leu Asn Leu Asp Val Ser Leu Gln Leu
        1265                1270                1275
Pro Ser Arg Ser Ser Lys Ile Thr His Arg Ile His Trp Glu Ser
```

|   |   |   |   |   |   |   |   |   |   |   |   |
|---|---|---|---|---|---|---|---|---|---|---|---|
|   |   |   | 1280 |   |   | 1285 |   |   | 1290 |   |   |
| Ala | Ser 1295 | Leu | Leu | Arg | Ser | Glu 1300 | Glu | Thr | Lys | Glu 1305 | Asn | Glu | Gly | Phe |

Thr Val Thr Ala Glu Gly Lys Gly Gln Gly Thr Leu Ser Val Val
1310            1315            1320

Thr Met Tyr His Ala Lys Ala Lys Asp Gln Leu Thr Cys Asn Lys
1325            1330            1335

Phe Asp Leu Lys Val Thr Ile Lys Pro Ala Pro Glu Thr Glu Lys
1340            1345            1350

Arg Pro Gln Asp Ala Lys Asn Thr Met Ile Leu Glu Ile Cys Thr
1355            1360            1365

Arg Tyr Arg Gly Asp Gln Asp Ala Thr Met Ser Ile Leu Asp Ile
1370            1375            1380

Ser Met Met Thr Gly Phe Ala Pro Asp Thr Asp Asp Leu Lys Gln
1385            1390            1395

Leu Ala Asn Gly Val Asp Arg Tyr Ile Ser Lys Tyr Glu Leu Asp
1400            1405            1410

Lys Ala Phe Ser Asp Arg Asn Thr Leu Ile Ile Tyr Leu Asp Lys
1415            1420            1425

Val Ser His Ser Glu Asp Asp Cys Leu Ala Phe Lys Val His Gln
1430            1435            1440

Tyr Phe Asn Val Glu Leu Ile Gln Pro Gly Ala Val Lys Val Tyr
1445            1450            1455

Ala Tyr Tyr Asn Leu Glu Glu Ser Cys Thr Arg Phe Tyr His Pro
1460            1465            1470

Glu Lys Glu Asp Gly Lys Leu Asn Lys Leu Cys Arg Asp Glu Leu
1475            1480            1485

Cys Arg Cys Ala Glu Glu Asn Cys Phe Ile Gln Lys Ser Asp Asp
1490            1495            1500

Lys Val Thr Leu Glu Glu Arg Leu Asp Lys Ala Cys Glu Pro Gly
1505            1510            1515

Val Asp Tyr Val Tyr Lys Thr Arg Leu Val Lys Val Gln Leu Ser
1520            1525            1530

Asn Asp Phe Asp Glu Tyr Ile Met Ala Ile Glu Gln Thr Ile Lys
1535            1540            1545

Ser Gly Ser Asp Glu Val Gln Val Gly Gln Gln Arg Thr Phe Ile
1550            1555            1560

Ser Pro Ile Lys Cys Arg Glu Ala Leu Lys Leu Glu Glu Lys Lys
1565            1570            1575

His Tyr Leu Met Trp Gly Leu Ser Ser Asp Phe Trp Gly Glu Lys
1580            1585            1590

Pro Asn Leu Ser Tyr Ile Ile Gly Lys Asp Thr Trp Val Glu His
1595            1600            1605

Trp Pro Glu Glu Asp Glu Cys Gln Asp Glu Glu Asn Gln Lys Gln
1610            1615            1620

Cys Gln Asp Leu Gly Ala Phe Thr Glu Ser Met Val Val Phe Gly
1625            1630            1635

Cys Pro Asn
1640

<210> SEQ ID NO 6
<211> LENGTH: 77
<212> TYPE: PRT
<213> ORGANISM: human

-continued

```
<400> SEQUENCE: 6

Ser Val Gln Leu Thr Glu Lys Arg Met Asp Lys Val Gly Lys Tyr Pro
1               5                   10                  15

Lys Glu Leu Arg Lys Cys Cys Glu Asp Gly Met Arg Glu Asn Pro Met
            20                  25                  30

Arg Phe Ser Cys Gln Arg Arg Thr Arg Phe Ile Ser Leu Gly Glu Ala
        35                  40                  45

Cys Lys Lys Val Phe Leu Asp Cys Cys Asn Tyr Ile Thr Glu Leu Arg
    50                  55                  60

Arg Gln His Ala Arg Ala Ser His Leu Gly Leu Ala Arg
65                  70                  75

<210> SEQ ID NO 7
<211> LENGTH: 76
<212> TYPE: PRT
<213> ORGANISM: human

<400> SEQUENCE: 7

Ser Val Gln Leu Thr Glu Lys Arg Met Asp Lys Val Gly Lys Tyr Pro
1               5                   10                  15

Lys Glu Leu Arg Lys Cys Cys Glu Asp Gly Met Arg Glu Asn Pro Met
            20                  25                  30

Arg Phe Ser Cys Gln Arg Arg Thr Arg Phe Ile Ser Leu Gly Glu Ala
        35                  40                  45

Cys Lys Lys Val Phe Leu Asp Cys Cys Asn Tyr Ile Thr Glu Leu Arg
    50                  55                  60

Arg Gln His Ala Arg Ala Ser His Leu Gly Leu Ala
65                  70                  75
```